United States Patent

Gray et al.

[11] Patent Number: 5,384,071
[45] Date of Patent: * Jan. 24, 1995

[54] CHIRAL LIQUID CRYSTAL COMPOUNDS

[75] Inventors: George W. Gray; David Lacey; Kenneth J. Toyne; Richard M. Scrowston; Ibrahim G. Shenouda, all of Hull; Lawrence K. M. Chan, Northolt, all of England; Adam Jackson, Trondheim, Norway; Madeline J. Bradshaw, Nr Newent, England; Victoria Brimmell, Earls Croome, England; Jennifer Constant, Powick, England; Edward P. Raynes, Malvern, England; Amarjit K. Samra, Bromsgrove, United Kingdom

[73] Assignee: Secretary of State for Defence in her Britannic Majesty's Government of the U.K. of Gt. Britian and Northern Ireland, London, England

[*] Notice: The portion of the term of this patent subsequent to Jul. 28, 2009 has been disclaimed.

[21] Appl. No.: 3,827

[22] Filed: Jan. 8, 1993

Related U.S. Application Data

[63] Continuation of Ser. No. 734,105, Jul. 24, 1991, abandoned, which is a continuation of Ser. No. 305,730, Feb. 1, 1989, abandoned.

[30] Foreign Application Priority Data

Jun. 23, 1986 [GB] United Kingdom ............ 8615316

[51] Int. Cl.$^6$ .............. C09K 19/30; C09K 19/12; C07C 255/00
[52] U.S. Cl. ............ 252/299.63; 252/299.01; 252/299.66; 252/299.6; 558/399
[58] Field of Search ......... 252/299.01, 299.6, 299.66, 252/299.63, 299.65; 558/399

[56] References Cited

U.S. PATENT DOCUMENTS

| | | | |
|---|---|---|---|
| 4,576,732 | 3/1986 | Isogai | 252/299.66 |
| 4,723,005 | 2/1988 | Huynh-Ba et al. | 252/299.6 |
| 4,777,280 | 10/1988 | Eldman et al. | 252/299.67 |
| 4,871,469 | 10/1989 | Reiffenrath et al. | 252/299.61 |
| 4,871,472 | 10/1989 | Krause et al. | 252/299.65 |
| 5,133,896 | 7/1992 | Coates et al. | 252/299.66 |

FOREIGN PATENT DOCUMENTS 61-243055 10/1986 Japan .

Primary Examiner—Philip Tucker
Attorney, Agent, or Firm—Nixon & Vanderhye

[57] ABSTRACT

This invention relates to novel chiral cyano-containing compounds suitable for use in ferroelectric smectic liquid crystal mixtures.

9 Claims, 8 Drawing Sheets

Route 1

R = alkyl or alkoxy

CHIRAL LIQUID CRYSTAL COMPOUNDS

This is a continuation of application Ser. No. 07/734,105, filed Jul. 24, 1991, now abandoned, which is a continuation of Ser. No. 07/305,730 filed Feb. 1, 1989, now abandoned.

This invention relates to novel chiral compounds suitable for use in ferroelectric smectic liquid crystal mixtures, and to such mixtures and devices which incorporate them.

Ferroelectric smectic liquid crystal materials use the ferroelectric properties of the chiral tilted smectic C, F, G, H, I, J and K phases (designated $S^*_C$ etc., the asterisk denoting chirality). The $S_C$ phase is generally the most useful, as it is the most fluid, and it is particularly desirable that the material shows an $S_A$ or nematic (denoted N) phase at temperatures above the chiral smectic phase, to assist surface alignment in a liquid crystal device. Ferroelectric smectic liquid crystal materials desirably have low viscosity, $S_C$ phases that persist over a broad temperature range which includes ambient temperature, chemical and photochemical stability, and in particular have a good spontaneous polarisation coefficient, Ps, measured in nC cm$^{-2}$. Such materials offer the possibility of very fast switched liquid crystal display devices.

Although some single compounds show all of the desirable properties outlined above, ferroelectric smectic liquid crystal materials in use today generally consist of a mixture of compounds which together show a chiral tilted smectic phase. Some of the compounds in such a mixture are of a type which either together or separately show a smectic phase (not necessarily being a chiral smectic phase), called a "smectic host", some are additives to improve the properties of the mixture, e.g. to suppress undesirable smectic phases and one or more is an optically active compound which induces the mixture to be chiral smectic, ideally with a good Ps. Such optically active compounds are called in the art "chiral dopants".

PCT patent application WO 86/00087 describes a series of optically active liquid crystal compounds that contain the chiral groups:

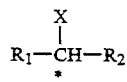

where X represents Cl, CN or CH$_3$ and R$_1$ and R$_2$ represent the residue of the molecule. All of the compounds described necessarily contain the phenyl-pyrimidine group,

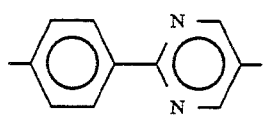

as the mesogenic unit. The pyridine ring is said to be particularly beneficial in the short molecules described as its molecular configuration increases intermolecular distances in the bulk, thus reducing the viscosity. Among the many compounds described are:

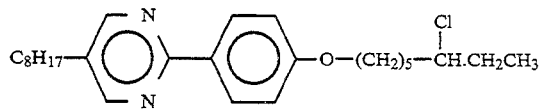

and

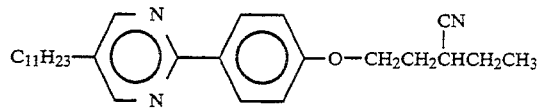

These two compounds do not show smectic phases by themselves.

PCT Application WO 87/05015 describes a series of compounds having a general formula

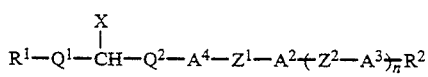

where X may be CN, Halogen or CH$_3$, R$^1$ and R$^2$ may be alkyl or alkoxy, Q$^1$, Q$^2$, Z$^1$ and Z$^2$ are linking groups and A$^1$, A$^2$ and A$^3$ are cyclic groups (e.g. phenyl etc.). No examples of compounds where X is CN are described, and a preference for X being halogen is expressed.

It is an object of the present invention to provide further compounds having advantageous properties for use in ferroelectric smectic liquid crystal mixtures. Other objects and advantages of the present invention will become apparent from the following account.

According to a first aspect of the invention there is provided a ferroelectric smectic liquid crystal mixture containing at least two compounds at least one of which is an optically active dopant compound having a general formula I below:

in which X is a group having a general structure:

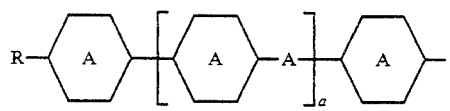

where R is selected from hydrogen or C$_{1\text{-}12}$ alkyl or alkoxy, each of the rings

is the same or different and is each independently selected from phenyl, halogen-substituted phenyl or trans cyclohexyl, A is selected from a single bond, COO or OOC, a is 0 or 1, Y is selected from COO or O, and B is alkyl containing 1-12 carbon atoms, cyclohexyl or a group

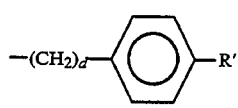

(5)

where d is 0 or 1 and R' is selected from hydrogen or $C_{1-12}$ alkyl or alkoxy.

Many compounds of Formula I are useful as chiral dopants in ferroelectric smectic liquid crystal mixtures with a host component.

The relative usefulness of various compounds of Formula I is one of the factors determining the structural and other preferences discussed herein.

In Formula I, R is preferably alkyl or alkoxy, containing 1 to 20 carbon atoms, especially n-alkyl or alkoxy containing 7 to 10 carbon atoms. Alkoxy is more preferred.

When —Y—CH(CH)— is present as —COO—CH(CN)— it is particularly preferred that B is cyclohexyl or alkyl.

When B is alky it may be n-alkyl, branched alkyl or optically active alkyl. The branching in the branched alkyl chain may be at any point so that when B is branched or optically alkyl it may have a structure B':

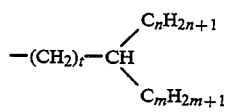

B' where t may be 0 or an integer 1–6 and n and m may be the same or different and have values 1–6. Preferably t is 0 or 1 and at least one of n or m is 1.

Preferred alkyl groups from which B may be selected are listed below in table 1.

TABLE 1

| | | |
|---|---|---|
| $CH_3$ | $CH(CH_3)_2$ | $CH_2CH(CH_3)_2$ |
| $C_2H_5$ | $CH(CH_3)C_2H_5$ | $CH_2CH(CH_3)C_2H_5$ |
| $C_3H_7$ | $CH(CH_3)C_3H_7$ | $CH_2CH(CH_3)C_3H_7$ |
| $C_4H_9$ | $CH(CH_3)C_4H_9$ | $CH_2CH(CH_3)C_4H_9$ |
| $C_5H_{11}$ | $CH(CH_3)C_5H_{11}$ | $CH_2CH(CH_3)C_5H_{11}$ |
| $C_6H_{13}$ | $CH(CH_3)C_6H_{13}$ | $CH_2CH(CH_3)C_6H_{13}$ |
| $C_7H_{15}$ | $CH(CH_3)C_7H_{15}$ | $CH_2CH(CH_3)C_2H_{15}$ |
| $C_8H_{17}$ | $CH(CH_3)C_8H_{17}$ | $CH_2CH(CH_3)C_8H_{17}$ |
| $C_9H_{19}$ | $CH(CH_3)C_9H_{19}$ | $CH_2CH(CH_3)C_9H_{19}$ |
| $C_{10}H_{21}$ | $CH(CH_3)C_{10}H_{21}$ | |

Particularly preferred alkyl groups in table 1 are underlined.

Some examples of preferred groups X in formula I, especially where —Y—W—CH(Z) is —COOCH(CN)— and with the preferred B groups are listed in table 2 below:

TABLE 2

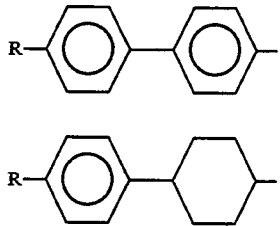

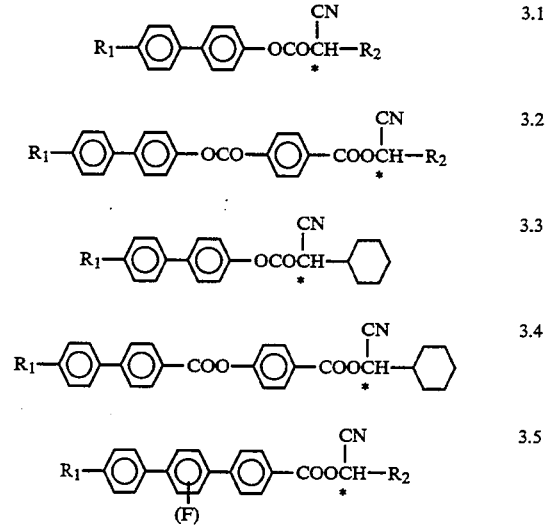

where R is n-alkyl or n-alkoxy, especially containing 3–12 carbon atoms. Of these structures 2.1 to 2.7 are preferred.

Some particularly preferred overall structures for the compound of formula I are therefore listed below in table 3

TABLE 3

TABLE 3-continued

where $R_1$ is $C_3$-$C_{12}$ n-alkyl or n-alkoxy and $R_2$ is $C_1$-$C_{12}$ n-alkyl or a branched or optically active alkyl group of structure B' especially those structures listed in table 1, and (F) indicates that a fluorine substituent may be present.

The chiral centre(s) in a compound of formula I may be of (R) or (S) configuration, and if the compound contains more than one chiral centre then preferably these are such as to induce the formation of S* phases having the same sign of Ps in a ferroelectric smectic mixture in which they are included.

Compounds of formula I in which the unit —Y—CH(CN)— is COO CH(CN) may be prepared for example by a number of widely applicable routes 1-5 shown schematically in FIGS. 1-5. Compounds of formula I in which —Y—CH(CH)— is —OCH(CN) may be prepared for example by route 6 shown in FIG. 6.

In routes 1-6 the group B is in some cases introduced into the compound of formula I using an alpha-hydroxy carboxylic acid of formula:

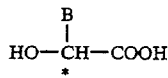

or an alpha-amino acid in formula:

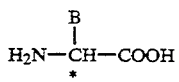

Routes 1-6 are of general suitability but are particularly suited to cases where B is alkyl, phenyl or cyclohexyl.

Some of these acids are commercially available in an optically pure enantiomeric form, e.g. the hydroxy carboxylic acids lactic acid (B=CH$_3$) and mandelic acid (B=phenyl), and the series of commercially available or naturally occurring amino acids, e.g. alanine, valine, leucine, isoleucine, butyrine, alloisoleucine, norvaline, norleucine and phenylalanine. As many such acids are of biochemical origin, they are often available in optically pure forms of one or more enantioners or antipodes, thus yielding optically pure products, whilst at the same time being relatively cheap. The use of these acids where possible is therefore preferred.

Alternatively these acids may be synthesized, to lead to a wider range of B-groups. The alpha-hydroxy acids may in fact be prepared from the corresponding amino acids by reaction of the amino acid with nitrous acid at low temperatures:

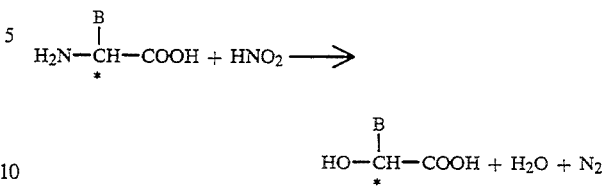

(e.g. "Tetrahedron" (1979), 35, 1603 and J.A.C.S. (1956) 78, 2428).

Other methods of preparation of alpha-hydroxy carboxylic acids are well known, for example as described in "Chemistry of Carbon Compounds" ed D. H. Dodd (pvb Elsevier) (1952), IB, p 780–781 (Ref 1) which lists 11 methods of preparation, including those where B may be straight chain, branched chain or optically active alkyl.

Similarly the amino acids having an appropriate B group may be synthesized be general well known methods, for example as described in Ref 1 p 813–817, where 13 methods for the synthesis of a wide range of amino acids is described, including those where B is straight chain, branched chain or optically active alkyl.

Preparation of a suitable alpha hydroxy or amino acid should therefore present no difficulty to the competent chemist. Where these preparation methods result in racemic mixtures of the optical enantiomers or antipodes they may be resolved by known methods, e.g. the use of brucine or stereospecific enzymic reactions.

When the amino acid used to pre pare the alpha-hydroxy acid or used directly e.g. in route 4 contains functional groups in its side chain B, these may be used to vary the structure of the group B.

For example serine, threonine and tyrosine contain —OH groups in their side chain, which enables the introduction of ester or ether linkages. Aspartic and glutamic acid contain —COOH groups in their side chain which also enable ester or other linkages to be introduced.

Examples of the types of unit which can be introduced into a compound of formula I using amino acids with functional groups in the side chain include:

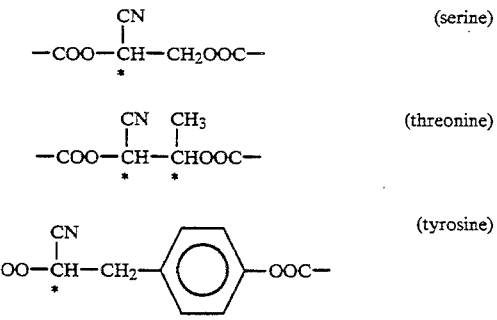

Similarly where routes 1-6 below require the use of a carboxylic acid of general structure R—X—CO$_2$H (where X is as defined in formula I) many of these are commercially available or else may be synthesised by well known general methods for example hydrolysis of the corresponding cyano compounds R—X—CN.

The individual steps of routes 1-6 are identified below.

Route 1

The steps are identified below:
(1)
  (i) 20% aqueous Cs$_2$CO$_3$ or K$_2$CO$_3$, methanol-water (9:1) pH 7.0
  (ii) Ph CH$_2$Br, DMF.
(2) N,N-dicyclohexylcarbodiimide (DCC), 4-(N-pyrrolidino)pyridine (N—PPy), CH$_2$Cl$_2$.
(3) 5% Pd/C, hydrogen, ethanol.
(4)
  (i) oxalyl chloride, benzene, dimethylformanide (DMF).
  (ii) aqueous ammonia, diglyme.
(5) SOCl$_2$, DMF.

Although it is illustrated for use with 4-alkyl- or alkoxybiphenyl-4'-carboxylic acid, Route 1 is generally suitable for all acids of formula R—X—CO$_2$H and particularly suitable for those groups X which contain rings

linked by single bond. By the use of lactic acid in step (1) B is caused to be methyl, but other homologous alpha-hydroxy carboxylic acids may be used to cause B to be other alkyl groups. By the use of mandelic acid, i.e.

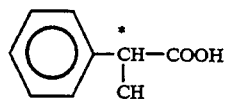

B may be caused to be phenyl.

Route 2

(1)

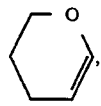

ethyl acetate, hydrogen chloride.
(2) KOH, ethanol, water
(3) similar to Route 1 steps (1) and (2)
(4) oxalic acid, 90% aqueous ethanol
(5) similar to Route 1 step (2)
(6) a series of steps analogous to route 1 steps (3)–(5)

As with roure 1, this route is generally applicable to compounds of formula I where one of the groups A in X is COO. By using other alpha-hydroxy acids, different groups B may be introduced into the molecule, as discussed above.

Route 3

(1) hydrogen, 5% Rh/Al$_2$O$_3$, methanol
(2) as route 1 step (1) using methanol solvent.
(3)

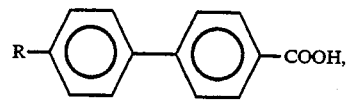

DCC, N—PPy, CH$_2$Cl$_2$ (R=alkyl or alkoxy)
(4) hydrogen, 5% Pd—C, ethanol.
(5)
  (i) (COCl)$_2$, benzene, DMF
  (ii) aqueous ammonia diglyme.
(6) SOCl$_2$, DMF.

Route 4

(1) Sodium Nitrite, H$_2$SO$_4$
(2) PhCH$_2$Br, DMF (Ph=phenyl)
(3) DCC, N—PPY, CH$_2$Cl$_2$
(4) H$_2$/Pd—C
(5) Oxalyl Chloride, DMF; NH$_3$
(6) SOCl$_2$, DMF Although route 4 is shown for a case where X is an R-biphenyl group, the method works equally well using any appropriate carboxylic acid in step (3).

In route 4, the group B in the starting amino acid is the group B of the final product. The amino acid may be used in any of its enantiomeric forms (a racemic amino acid would lead to a racemic product). The residue B in the starting amino acid may itself contain an asymmetric carbon atom, for example in the case of isoleucine.

Various other compounds wherein the unit —YWCH(Z)— is —COO CH(CN)— may be made via routes derived from routes 1-4 above. For example compounds of structure 3.4 may be made by esterifying the product of step 3(2) with the acid produced in step 2(2) and proceeding via a route analogous to steps 2(3) to 2(6).

Compounds of structure 3.5 may be prepared via route 5 shown in FIG. 5 starting from the commercially available biphenyl and bromobenzoic acid.

Route 5

(1) When the F is present: n—BuLi, ether, −35° C., 20 min, ZnCl$_2$, THF, N$_2$. When the F is not present: n—BuLi, ether, −5° to −10° C., 45 min; ZnCl$_2$, THF, N$_c$.
(2) An appropriate alcohol or phenol, e.g. the product of steps 4(2) or 3(2), DCC, N—PP$_y$, CH$_2$Cl$_2$.
(3) Pd[Ph$_3$P]$_2$Cl$_2$, di-isobutylaluminium hydride, THF N$_2$.

The product of step 5(3) may then be converted to the cyano compound e.g. of structure 3.5 by a method analogous to steps 4(4)–4(6).

Route 6

(1) esterification of the alpha-hydroxy acid using e.g. DCC method. Some such esters may be commercially available, e.g. ethyl lactate.
(2) toluene-4-sulphonyl chloride, pyridine.
(3) K$_2$CO$_3$, acetonitrile.
(4) KOH, ethanol, H$_2$O.
(5) and (6), as steps 4(5) and (6)

Compounds of formula I may be used as optically active components of ferroelectric smectic liquid crystal mixtures, i.e. as chiral dopants. When used as components of such mixtures compounds of formula I, particularly the preferred compounds referred to above, may offer the following advantages.

(i) They may show a very high spontaneous polarisation coefficient (Ps). This may conveniently be expressed in terms of the extropolated Ps, i.e. the Ps of the mixture extropolated to 100% of the compound of formula I. This means that a quite small amount of the compound of formula I need be included in the mixture.

(ii) They may induce the appearance of chiral smectic phases in the mixture having a very long helical pitch. This may more conveniently be assessed by measuring the chiral nematic N* pitch they induce when mixed with a nematic liquid crystal materal. A long pitch is desirable as in some ferroelectric smectic liquid crystal devices the pitch should be as close as possible to the spacing of the electrodes, and in practice the difficulty of manufacture increases with decreasing electrode spacing.

(iii) Chiral smectic mixtures containing them may show Sc* phases which persist over a wide temperature rnage, including room temperature.

(iv) They are compatible with many hosts and additives for example those discussed below.

(v) They may offer the possibility of very high switching speeds, which is of advantage in for example video screen type applications. This is partly due to (i) above in that many known chiral dopants are viscous and cause mixtures containing them to be viscous. The good Ps induced by compounds of formula I means that relatively little need be used and hence there is little adverse effect on viscosity.

(vi) It is often possible to obtain compounds of formula I in both D(+) and L(+) enantiomeric forms as both enantioneric forms of the starting amino acid for their preparation may be available. This makes the pitch of mixtures containing them to be particularly easy to "compensate" (see below) by including opposite-twisting enantiomers of the compounds of formula I in the mixture.

A ferroelectric smectic liquid crystal mixture according to the invention contains at least one compound of formula I. Typically the mixture will contain 1–20% by weight of the compound of formula I, e.g. around 10% or less. Generally the Ps of the mixture is proportional to the amount of chiral dopant present.

The mixture should contain one or more compounds which either separately or together shown an Sc phase. Such compounds are known as smectic hosts.

A large number of classes of compounds which may be used as smectic hosts are known, and some examples of suitable classes are listed in table 4. Of these compounds those of formula 4.1, 4.2, 4.3, and 4.8 are preferred, especially where $R^A$ and $R^B$ independently contain 5–10 carbon atoms. It is particularly preferred to use a mixture of two or more members, e.g. homologues, of the same class for example to reduce the melting point.

These preferred hosts allow the possibility of Sc mixtures showing an Sc phase persisting over a wide temperature range including room temperature, and also an $S_A$ phase at a temperature above the Sc, to assist in alignment of the liquid crystal material. Typically the mixture will contain 40–99% of host compounds, e.g. around 80%.

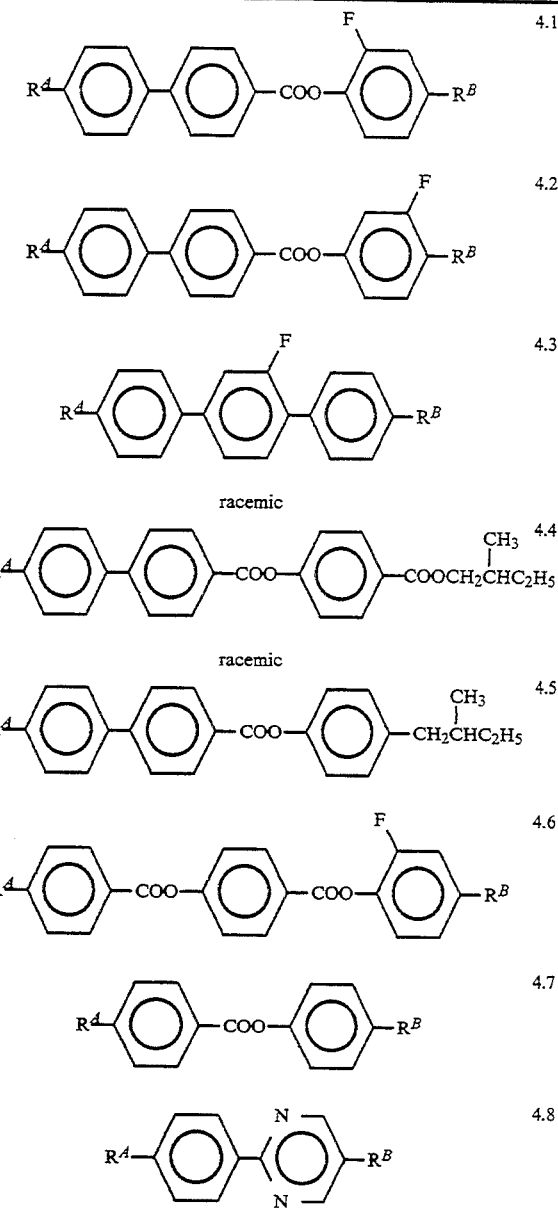

TABLE 4 where $R^A$ and $R^B$ are $C_{1-12}$ n-alkyl or n-alkoxy.

Additives in such a mixture may serve a number of functions. One such function is as "pitch compensators." "Pitch compensation" is the inclusion in the ferroelectric smectic mixture of two or more compounds which induce the appearance of helical smectic phases of opposite twist sense. In such a case the compounds will unwind the helical phase induced by the other. This may be used to produce along pitch helical smectic phase, and by the controlled use of appropriate quantities of the two compounds the pitch of the mixture may be closely controlled.

In mixtures according to the invention, pitch compensation may be achieved conveniently by using opposite-twisting compounds of formula I as discussed above which may be different compounds of formula I or enantiomers e.g. the L(+) and S(+) forms of the compound

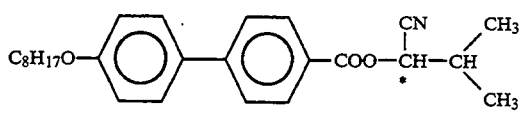

Alternatively or additionally other optically active additives may be used, for example the amides described in PCT/GB 87/00223, e.g. any of those listed in table 6 thereof, or the terphenyls described in UK Patent Application 8703103, the latter being particularly suitable when the host includes one or more compounds of formula 4.3.

Examples of pitch compensators of these two types include the compounds:

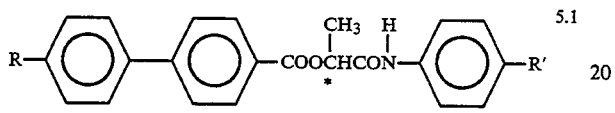

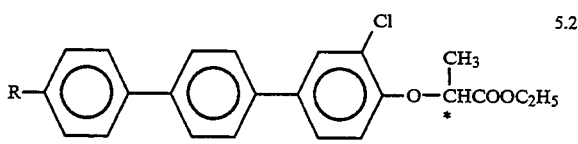

where R and R' are independently $C_{1-12}$ n-alkyl or n-alkoxy. F' is preferably $CH_3$. Many other pitch compensating additives will be apparent to those skilled in the art. For example when the host contains one or more compounds of formula 4.1 or 4.2, a suitable pitch compensator may be a compound of formula 4.1 or 4.2 where $R^B$ or/and $R^A$ are optically active alkyl or alkoxy.

Additives may be used to encourage the appearance of an $S_A$ phase at a temperature above that at which the $S_C^*$ phase persists, to assist in alignment of the $S_C^*$ phase during assembly of the service. When the host consists largely of compounds of formula 4.1 or 4.2, preferred additives to achieve this have a formula:

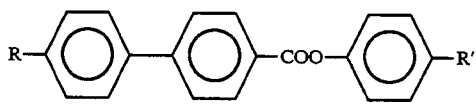

where R and $R^1$ are independently n-alkyl or n-alkoxy containing 1-12 carbon atoms, especially 5-9.

Additives may alternatively serve the function of suppressing undesirable smectic phases such as $S_A$ or $S_B$ so that these appear, if at all, as far as possible from the working temperature range. A preferred class of additives fulfilling this function are the esters of formula:

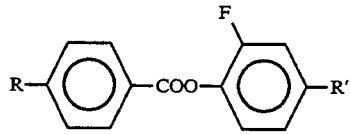

where R and $R^1$ are independently n-alkyl or n-alkoxy containing 1-12 carbon atoms, especially 5-9. Compounds of formula 4.8 may also be used as additives to suppress undesirable smectic phases in mixtures where they are not used as hosts.

Additives may also improve other properties of the mixture, for example to increase the switching speed. Compounds which do this include those which contain a

group, for example those of general formula

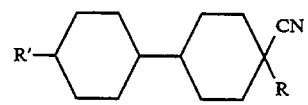

or

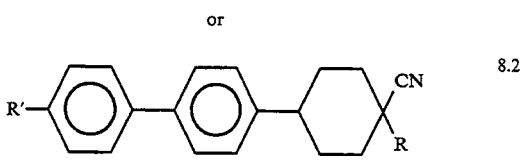

where R and $R^1$ are independent alkyl groups especially containing 3 to 10 carbon atoms.

Other known additives may be included, for example to improve viscosity, melting point or other properties.

Typically a mixture according to the invention may contain 0-50wt % of additives, preferably 0-20%. Only minute amount of pitch compensators may be necessary, e.g. less than 1 wt % of the tight twisting compound 5.1 where R is $C_{10}H_{21}$ and $R^1$ is $CH_3$, and preferably no more than about 10 wt % of compounds such as 6, 7, 8.1 or 8.2.

A mixture according to the invention may be used in any of the known types of ferroelectric smectic liquid crystal electro-optic device, and a device incorporating such a mixture is another aspect of the invention.

BRIEF DESCRIPTION OF THE DRAWINGS

The invention will now be described by way of example only with reference to the accompanying drawings, which show.

Figure 1:
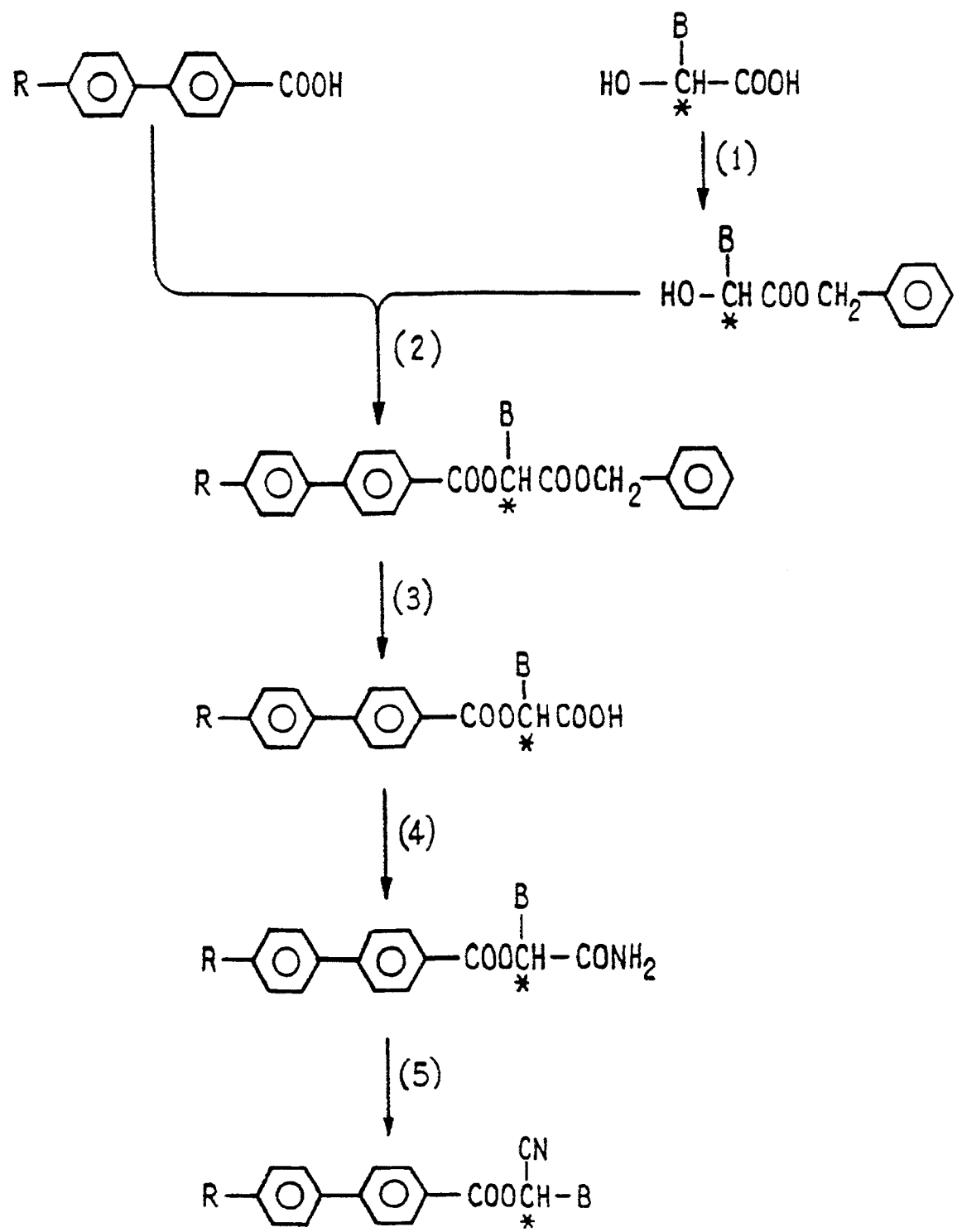
FIGS. 1-6 preparative routes for compounds of the invention.
Figure 2:
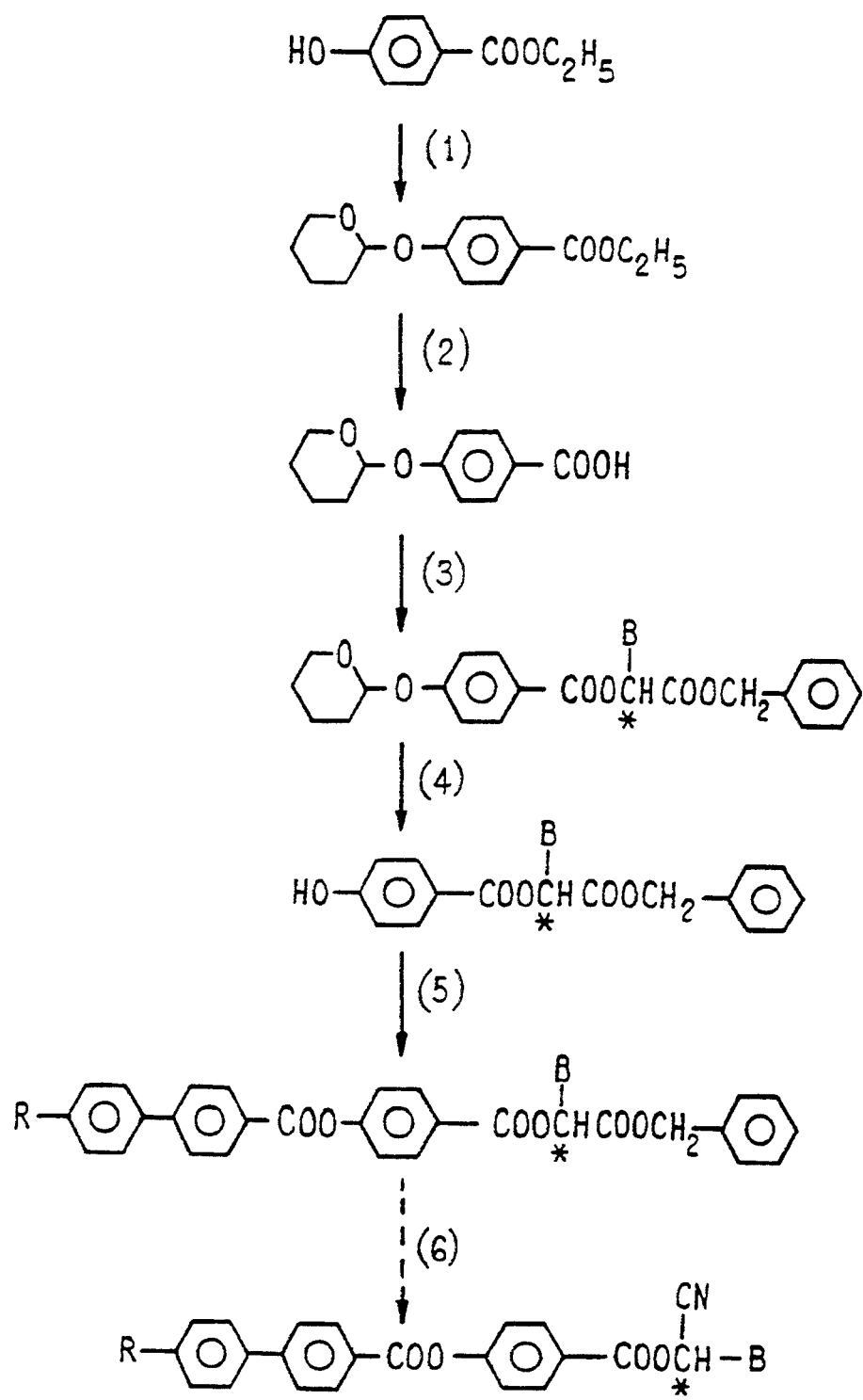
Figure 3:
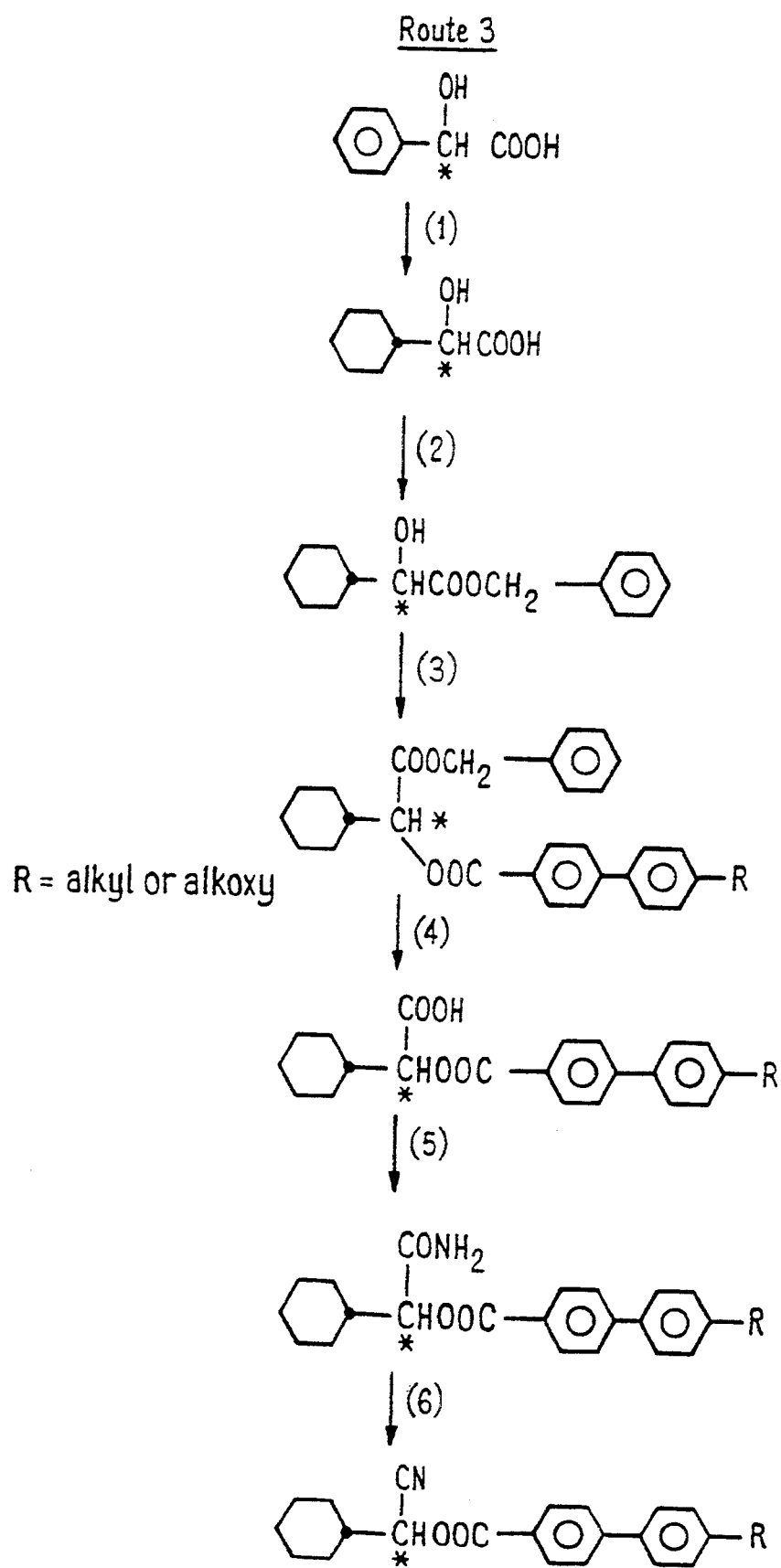
Figure 4:
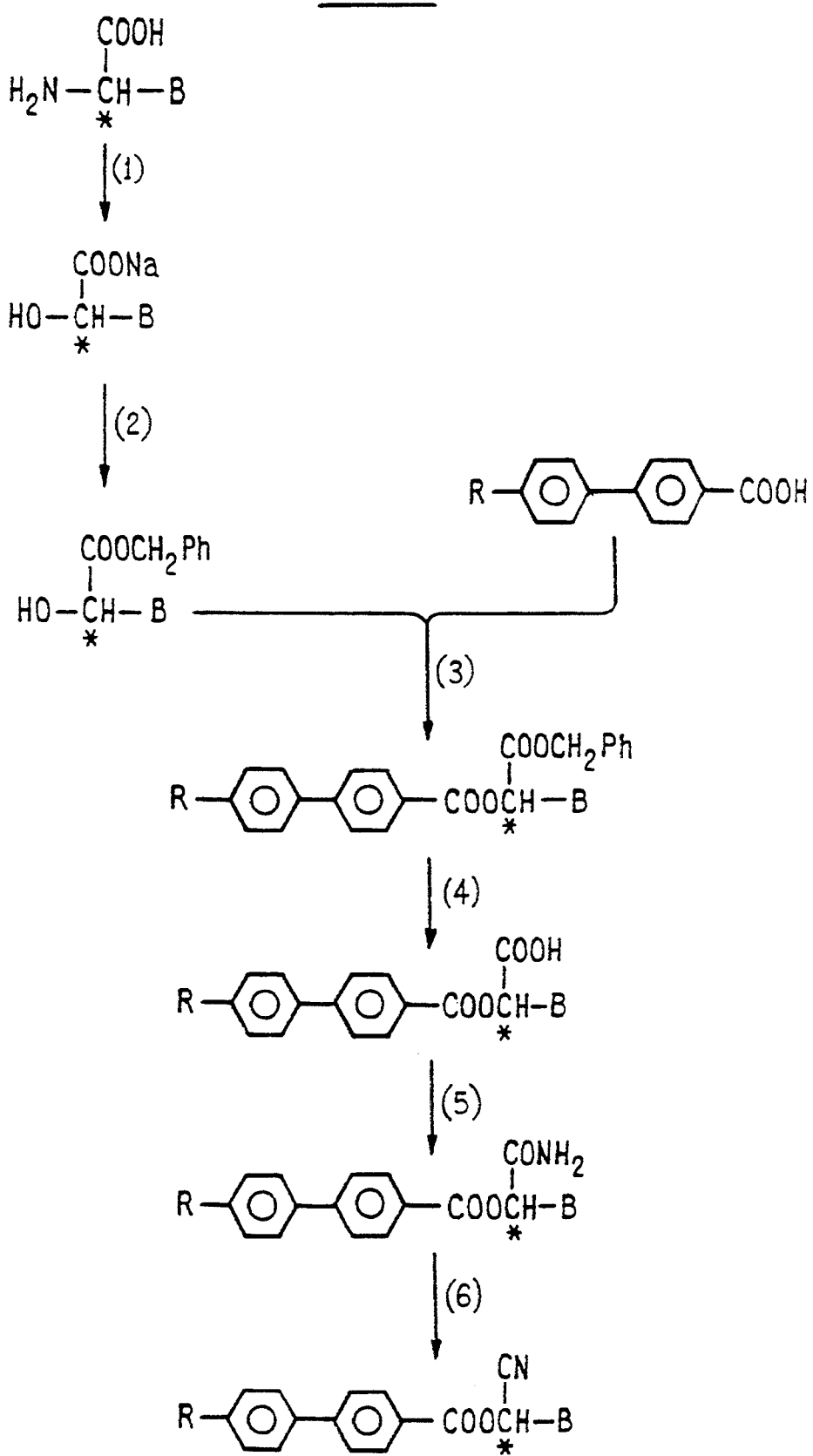
Figure 5:
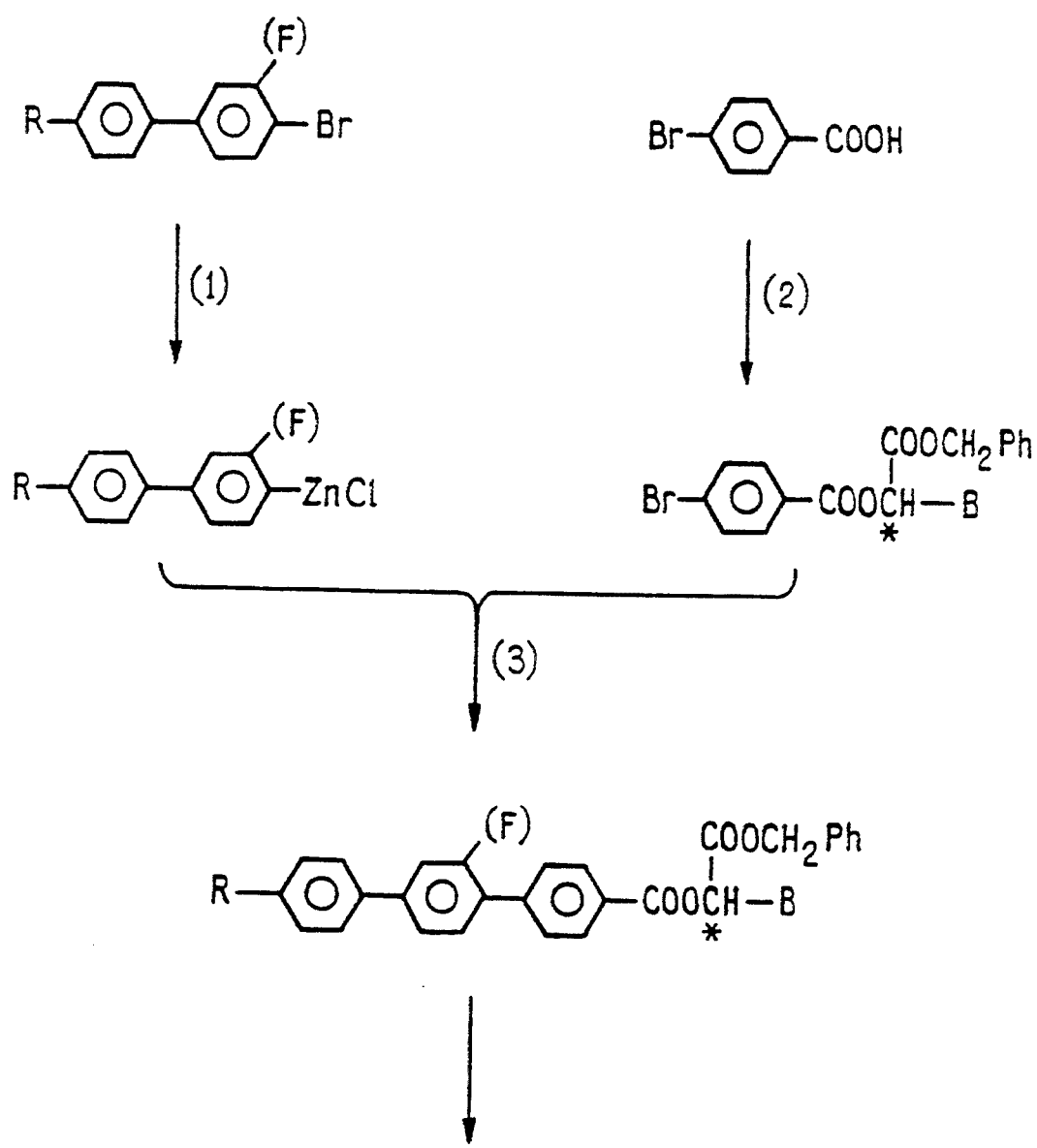
Figure 6:
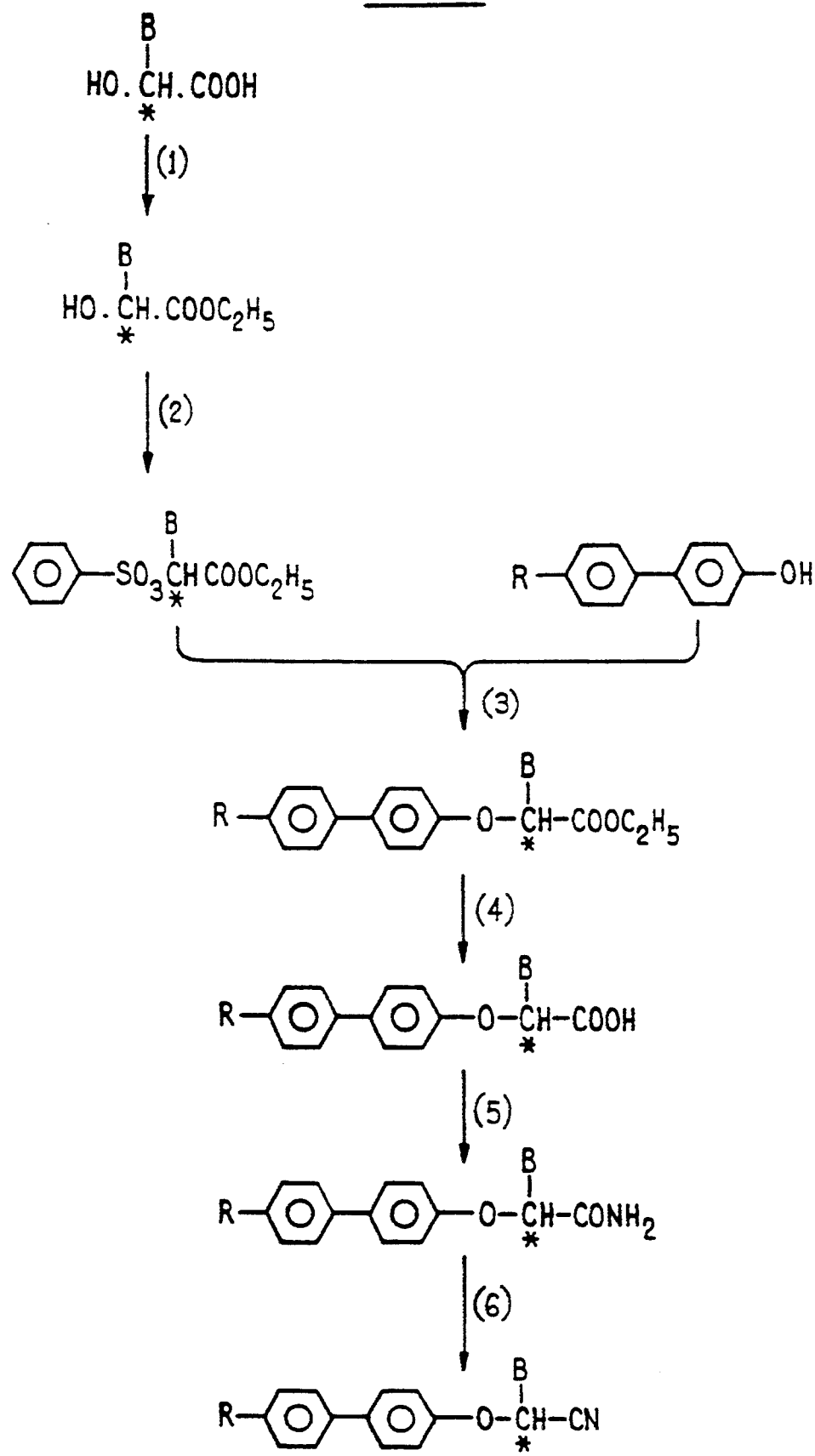

Examples of methods of preparation of compounds of Formula 1, of ferroelectric smectic liquid crystal materials including them and of a liquid crystal electro-optic display device using them follow.

EXAMPLE 1

Preparation of;

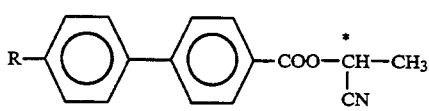

using Route 1

Step 1(1)

S-(+)-Lactic acid (18.0 g) (previously redistilled from commercial product) was dissolved in methanol (360 ml), and water (40 ml) was added. The solution was trated to pH 7-0 with 20% aqueous caesium carbonate (ca 160 ml). The solvent was removed under reduced pressure at 50° C. and the residue was re-evaporated twice from DMF (2×100 ml) at the same temperature. The white solid caesium salt obtained was stirred with benzyl bromide (34.2 g) in DMF (300 ml) for 15 hours. The CsBr was then filtered off, the filtrate was concentrated and then ether was added to the residue (150 ml). The organic layer was washed successively with water (100 ml), saturated Na NHO$_3$ (500 ml) and water (100 ml) and finally dried (MgSO$_4$). After removal of the solvent the residual liquid was distilled under reduced pressure to afford the product as coulourless liquid (yield 28.8 g; 80%), bp 96° C./0.05 mm Hg[α]$_D^{24}$−12.9°.

Step 1(2)

To a stirred mixture of 4-R-biphenyl-4'-carboxylic acid (10.8 g), S-(−)-benzyl lactate (5.9 g) prepared as in step 1(1) above, and N—PPy (0.49 g) in sieve-dried (CH$_2$Cl$_2$ (250 ml) was slowly added a solution of DCC (7.5 g) in sieve dried CH$_2$Cl$_2$ (50 ml). The mixture was stirred for 5 h at room temperature. The N,N-dicyclohexyl urea was filtered off and the filtrate was washed successively with water (100 ml), 5% aqueous acetic acid (100 ml), water (2×100 ml) and finally dried (MgSO$_4$). After removal of the solvent, the crude diester was purified by column chromatography using silica gel and (4:1) dichloromethane: petroleum fraction (bp 60°-80° C.) as eluent. The product was recrystallised from ethanol The properties of compounds prepared in this way were:

R=C$_9$H$_{19}$: mp 60.5° C.; [α]$_D^{24}$+21.6°.
R=C$_{10}$H$_{21}$O: mp 85° C.; [α]$_D^{24}$+24.2°.
R=C$_8$H$_{17}$O: mp 62.5° C.; [α]$_D^{24}$+24.7°.

Step 1(3)

The product of step 1(2) (10–12 g) was dissolved in ethyl acetate (150 ml). 5% Pd on charcoal (200 mg) was added and the mixture was stirred under an atmosphere of hydrogen overnight. After hydrogenation (500 ml of hydrogen was consumed) was completed, the catalyst was filtered off and the filtrate was evaporated to dryness. The colourless solid residue was recrystallised from petroleum fraction (bp 60°-80° C.) to give the carboxylic acid as colourless needles.

R=C$_9$H$_{19}$: mp 106° C.; [α]$_D^{24}$+32.3°.
R=C$_{10}$H$_{21}$O: mp 115° C.; [α]$_D^{24}$+35.0°.
R=C$_8$H$_{17}$O: mp 126° C.; [α]$_D^{24}$+40.8°.

Step 1(4)

The carboxylic acid of step 1(3) (0.01 mol) was initially converted into the acid chloride by reacting with oxalyl chloride (0.02 mol) and sieve-dried DMF (3 drops) in sodium-dried benzene (50 ml) for 3 hours at room temperature. The excess of oxalyl chloride and the solvent were removed by distillation under reduced pressure. The crude acid chloride residue was dissolved in diglyme (20 ml) and then an aqueous solution of ammonia (25 ml, d=0.88) was added dropwise with vigorous stirring. After the addition the reaction mixture was stirred for 1½ hours at room-temperature. The reaction mixture was then diluted with cold water (200 ml) and the product was filtered off, washed with excess water and then finally dried in air. The product was crystallised from petroleum fraction (bp 80°-100° C.) to yield the amide as a white powder.

R=CH$_9$H$_{19}$: yield=2.6 (66%); mp 145° C.; [α]$_D^{24}$+48°.
R=C$_{10}$H$_{21}$O: yield=1.8 g (47%); C$_1$ 130 C$_2$ 143 I[α]$_D^{24}$+43.4.

Step 1(5)

A mixture of redistilled thionyl chloride (0.063 mol) and sieve-dried DMF (10 ml) was added dropwise to a vigorous stirred solution of the product of step 1(4) (0.0063 mol) in DMF (30 ml). After the addition the reaction mixture was stirred at room temperature for 2 hours, poured onto ice-water (200 ml) and the product extracted into ether (2×100 ml). The combined ether extracts were washed with saturated aqueous sodium hydrogen carbonate (2×100 ml), followed by water (100 ml) and finally dried (Mg SO$_4$). After the removal of the solvent the product was purified by column chromatography on silica gel, eluting with a 3:1 mixture of chloroform: petroleum fraction (bp 60°-80° C.). The appropriate fractions containing the product were concentrated and recrystallised from 95% aqueous ethanol to yield the final nitrile product as a white crystalline solid.

R=C$_9$H$_{19}$: yield=1.7 g (71%), mp 55.0° C.; $_D^{24}$+55°.
R=C$_{10}$H$_{21}$O: yield=0.92 g (62%), mp 98.5° C.; $_D^{24}$+6.5°.

EXAMPLE 2

Preparation of:

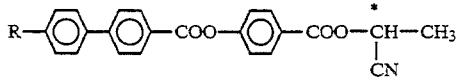

using Route 2

Step 2(1)

To a stirred mixture of the ethyl 4-hydroxybenzoate (0.063 mol) and 2,3-dihydropyran (0.25 mol) in ethyl acetate (80 ml) was added dropwise a saturated solution of hydrogen chloride in ethyl acetate (5 ml). After the addition the reaction mixture was stirred for 24 hours at room temperature. The mixture was then washed with 10% aqueous sodium hydroxide (2×50 ml), followed by water (2×50 ml) and finally dried (MgSO$_4$). After removal of the solvent by distillation under reduced pressure the oily residue was purified by distillation under reduced pressure to give a colourless liquid.

Yield=10.4 g (66%) bp 120°-25° C./0.1 mm Hg (Short path distillation).

Step 2(2)

A solution of potassium hydroxide (0.076 mol) in water (10 ml) was added to a solution of the product of step 2(1) (0.038 mol) in C$_2$H$_5$OH (50 ml). The mixture was heated under reflux for 3 hours. On cooling, the solvent was removed by distillation under reduced pressure. Ice-water (100 ml) was added to the residue, and whilst being vigorously stirred and cooled below 10° C., 50% aqueous hydrochloric acid was added until the acidity of the mixture reached about pH 3. The product was extracted into ethyl acetate (2×100 ml) and the combined organic extracts were washed with water (2×100 ml) and dried (Mg SO$_4$). After removal of the solvent the crude material was crystallised from 2:1 toluene: Petroleum fraction (bp 80°-100° C.) to give the carboxylic acid as white crystals.

Yield=5.8 g (69%), decomposed on heating at 145° C.

Step 2(3)

This step was performed using the product of Step 1(1) (the benzyl ester of S-(+)-lactic acid) in a method analogous to step 1(2) (esterification of the lactic acid alpha-hydroxy group) using the carboxylic acid prepared in step 2(2). The product as obtained by column chromatography was used in subsequent steps without further purification.

The product had mp below 20° C.; $[\alpha]_D^{24}+18°$.

Step 2(4)

A solution of oxalic acid (0.0031 mol) in water (8 ml) was added to the product of step 2(3) (0.0156 mol) and the while was gently refluxed for 2 hours. The solution was cooled and the solvent was removed by distillation under reduced pressure. The residue was heated with water (50 ml) and the product was extracted into ether (2×50 ml), and the combined ether extracts were washed with water (50 ml) and dried (Mg SO₄). The oily crude product (single spot on tlc) was used for step 2(5) without further purification.

Yield=4.56 g (95%); $[\alpha]_D^{24}+15°$.

Step 2(5)

This step was performed using a DCC method of esterification analogous to that used in step 1(2) but using the phenol product of step 2(4) instead of the benzyl lactate for esterification with the 4-R-biphenyl-4'-carboxylic acid.

R=C₉H₁₉O;   C   104°(S_c90°)   S_A133.5°Ch 135.5°I $[\alpha]_D^{24}+6.9°$.

Step 2(6)

This step involved three separate steps (denoted (a), (b) and (c) below) analagous to steps 1(3), 1(4) and 1(5). The properties of the products of each of these separate steps for R=C₉H₁₉O are as follows:

(a) C149 S_A 198 I; $[\alpha]_D^{24}+17.6°$.
(b) C180 S_A 198 I; $[\alpha]_D^{24}+15.0°$.
(c) C121 S_C 132 S_A 181 I; $[\alpha]_D^{24}-2.9°$.

EXAMPLE 3

Preparation of

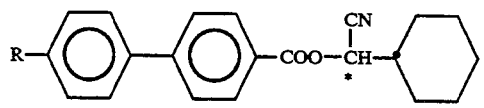

Step 3(1)

(ref Stocker J Org Chem 27, 2288, (1962)).

A mixture of L-(+)-mandelic acid (10 g), acetic acid (1 ml) and 5% Rh/Al₂O₃ (1.95 g) in methanol (70 ml) was stirred under hydrogen (30 atm) until the uptake of hydrogen was complete. The catalyst was filtered off and the solvent was removed. Recrystallisation from carbon tetrachloride gave the cyclohexyl compound as a white crystalline solid.

Yield=85%; mp=128° C.

Step 3(2)

(ref S. S. Wang J-Org-Chem, 41, 3258, (1976)

A solution of the product of step 3(1), (5 g) in the minimum volume of 4:1 ethanol: water was titrated to pH 7 with aqueous caesium carbonate (20% W/V). The solution was then evaporated to dryness and the last traces of water were removed by co-distillation with sodium-dried benzene (2×100 ml). The residue was dissolved in sieve-dried DMF (100 ml) and benzyl bromide (5.3 g) was added, with stirring. Stirring was continued for 12 hours after which time the precipitate caesium bromide was filtered off and the solvent was removed under reduced pressure. Water was added to the residue, and the product was extracted into ethyl acetate (100 ml) and the extracts were dried (MgSO₄). Purification was by column chromography on silica gel using 1:3 ethyl acetate/petroleum fraction (bp 60°-80° C.) or eluent, followed by recrystallisation from petroleum fraction (bp 40°-60° C.).

Yield=79%; mp 47° C.

Step 3(3)

(ref A. Hassner, V. Alexanian, Tetrahedron, 46, 4475, (1978))

A solution of the appropriate carboxylic acid, in this case n-4-octyloxybiphenyl-4-octyloxybiphenyl-4'-carboxylic acid (10 m mol), the product of step 3(2) (11 m mol), DCC(11 m mol) and N—PPy (1 mol) in sieve-dried dichloromethane (50 ml) was stirred with exclusion of moisture. The progress of the reaction was followed by tlc on silica gel, eluting with 2:1 chloroform: petroleum fraction (bp 60°-80° C.). The mixture was filtered off and the filtrate was washed successively with water (3×50 ml), 5% acetic acid (3×50 ml) and again water (3×50 ml), then finally dried (MgSO₄). The product (an oil) was purified by column chromatography on silica gel, eluting with 2:1 chloroform: petroleum fraction (bp 60°-80° C.) to give the product as colourless liquid.

Yield=67%; $[\alpha]_D^{25}+5.3°$.

Step 3(4)

A mixture of the product of step 3(3) and (1 g) and 5% Pd—C in ethanol (25 ml) was stirred under an atmosphere of hydrogen until uptake of the gas had ceased. The catalyst was filtered off and the solvent removed by distillation under reduced pressure. Purification of the crude product was by column chromatography on silica gel, eluting with a 5:1 chloroform:methanol. Recrystallisation from petroleum fraction (bp 60°-80° C.) gave the carboxylic acid as a white crystalline solid.

Yield=96%: mp=83° C.; $[\alpha]_D^{25}-39.5°$.

Step 3(5)

A suspension of the product of step 3(4) (0.5 g) in a mixture of sodium-dried benzene (25 ml), oxalyl chloride (0.25 g) and DMF (one drop) was stirred for 2 hours. The solvent was removed by distillation under reduced pressure and the residue was dissolved in dry diglyme (50 ml). Aqueous ammonia (d=0·88, 10 ml) was added to this solution was vigorous stirring during 30 min, and stirring was continued for a further 30 minutes. The mixture was diluted with water (100 ml) and the precipitated amide was filtered off. Recrystallisation from 4:1 ethanol:water gave the product as a white powder.

Yield=82%, mp 126° C.

Step 3(6)

A solution of the product of step 3(5) (0.47 g), thionyl chloride (1.2 g) and dry DMF (30 ml) was stirred for 8 hours. The reaction mixture was then poured into water (50 ml) and the nitrile was extracted into ether (3×50 ml). The combined ether extracts were washed with saturated sodium hydrogen carbonate solution and dried (MgSO$_4$). Purification of the crude nitrile was by column chromatography on silica gel, eluting with 1:5 ethyl acetate:petroleum fraction (6 p 60°-80° C.). Recrystallisation from 4:1 ethanol:water gave the nitrile as a white crystalline solid.

Yield=78%, mp 58.5° C.; $[\alpha]_D^{25}$ −10.5.

EXAMPLE 4

Ferroelectric smectic liquid crystal mixture containing compounds of Formula I in hosts which are compounds of formula 4.1

Mixture A

Host:

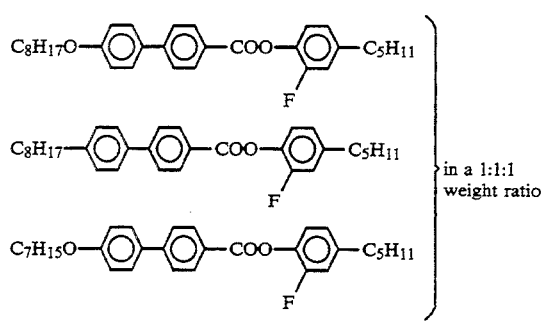

in a 1:1:1 weight ratio

Dopant:

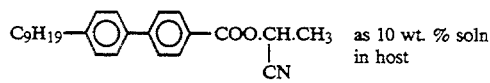

as 10 wt. % soln in host

Transition temperatures; S?ca. 40 S$_C$ 66.8 S$_A$ 111.3 N 134.7 I.

| | Ferroelectric properties: | |
|---|---|---|
| Temperature (°C.) | Extrapolated Ps (nC cm$^{-2}$) | Tilt angle of S$_C$ phase (°) |
| 65 | 56 | 2.5 |
| 60 | 133 | 5.5 |
| 40 | 315 | 9.5 |

The extrapolated pitch of the S$_C$ phase of the mixture was 0.201 μm.

Mixture B

Host:
The same host mixture as in mixture A plus 10 wt. % of

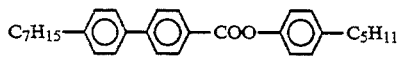

Dopant:

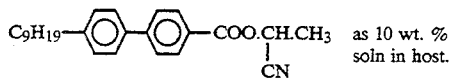

as 10 wt. % soln in host.

Transition temperatures: S?45 S$_C$ 56.1 S$_A$ 115 N 134.8 I.

| | Ferroelectric properties: | |
|---|---|---|
| Temperature (°C.) | Extrapolated Ps (nC cm$^{-2}$) | Tilt angle of S$_C$ phase (°) |
| 55 | 15.5 | 0.75 |
| 50 | 133 | 4.3 |

The extrapolated pitch of the S$_C$ phase of the mixture was 0.291 μm. Mixtures C to G below were all based on a smectic host having a composition:

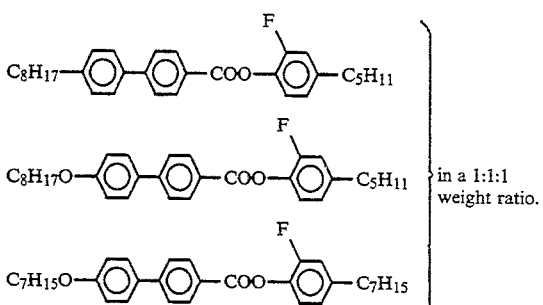

in a 1:1:1 weight ratio.

Mixture C 90 wt. % host mixture 10 wt. % 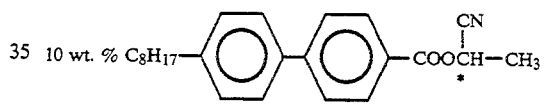

Transition temperatures: S$_C$—S$_A$ 64°, S$_A$—Ch 109.6°, CH—I 135.2°-136.8° (S$_C$ at room temp.)

Mixture C (contd.)

| Ferroelectric properties: | | | |
|---|---|---|---|
| Temperature °C. | Ps nCcm$^{-2}$ | Temperature °C. | Ps nCcm$^{-2}$ |
| 31 | 3.47 | 45 | 21.52 |
| 32 | 6.94 | 50 | 18.75 |
| 33 | 29.17 | 55 | 13.89 |
| 34 | 29.86 | 60 | 9.37 |
| 35 | 28.47 | 63 | 4.34 |
| 40 | 24.30 | | |

Mixture D 90 wt. % host mixture 10 wt. % 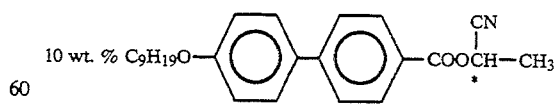

Transition Temperatures: S—S$_C$32°, S$_C$—S$_A$ 81° C., S$_A$—Ch 118.8°, Ch—I 139.2°-140.5°.

| Ferroelectric properties: | | | |
|---|---|---|---|
| Temperature °C. | Ps nCcm$^{-2}$ | Temperature °C. | Ps nCcm$^{-2}$ |
| 31 | 18.75 | 50 | 27.08 |

| Ferroelectric properties: | | | |
|---|---|---|---|
| Temperature °C. | Ps nCcm$^{-2}$ | Temperature °C. | Ps nCcm$^{-2}$ |
| 32 | 44.44 | 55 | 25.00 |
| 33 | 40.28 | 60 | 21.53 |
| 34 | 38.89 | 65 | 18.40 |
| 35 | 36.81 | 70 | 14.93 |
| 40 | 33.33 | 75 | 10.41 |
| 45 | 30.56 | 80 | 1.39 |

Mixture E 60 wt. % host mixture

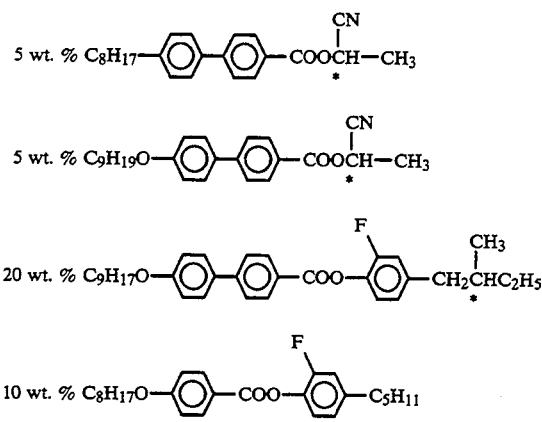

5 wt. % $C_8H_{17}$—〇—〇—COOCH(CN)—CH$_3$ 5 wt. % $C_9H_{19}O$—〇—〇—COOCH(CN)—CH$_3$ 20 wt. % $C_9H_{17}O$—〇—〇—COO—〇(F)—CH$_3$CH$_2$CHC$_2$H$_5$ 10 wt. % $C_8H_{17}O$—〇—COO—〇(F)—C$_5$H$_{11}$

Mixture E. (contd.)

Transition temperatures: S—S$_C$ 11°, S$_C$—S$_A$ 58.7°, S$_A$—N 100°, Ch—I 124°–125.4°.

| Ferroelectric properties: | | | |
|---|---|---|---|
| Temperature °C. | Ps nCcm$^{-2}$ | Temperature °C. | Ps nCcm$^{-2}$ |
| 10 | 48.61 | 40 | 22.92 |
| 15 | 41.67 | 45 | 19.79 |
| 20 | 36.81 | 50 | 15.63 |
| 25 | 33.33 | 55 | 9.55 |
| 30 | 29.86 | 58 | 2.78 |
| 35 | 25.69 | | |

Mixture F 75 wt % host mixture

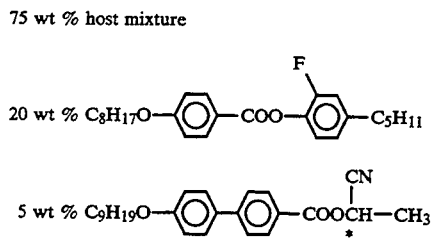

20 wt % $C_8H_{17}O$—〇—COO—〇(F)—C$_5H_{11}$ 5 wt % $C_9H_{19}O$—〇—〇—COOCH(CN)—CH$_3$

Transition temperatures: S$_C$—S$_A$ 62.56°, S$_A$—Ch 81.4°, Ch—I 121°–123.2° (room temp S$_C$).

| Ferroelectric properties: | | | |
|---|---|---|---|
| Temperature °C. | Ps nCcm$^{-2}$ | Temperature °C. | Ps nCcm$^{-2}$ |
| −5 | 22.2 | 35 | 10.76 |
| 0 | 18.75 | 40 | 9.72 |
| 5 | 17.71 | 45 | 8.51 |
| 10 | 16.67 | 50 | 7.46 |

| Ferroelectric properties: | | | |
|---|---|---|---|
| Temperature °C. | Ps nCcm$^{-2}$ | Temperature °C. | Ps nCcm$^{-2}$ |
| 15 | 15.63 | 55 | 5.90 |
| 20 | 14.24 | 60 | 3.75 |
| 25 | 13.19 | 62 | 2.57 |
| 30 | 12.15 | | |

Mixture G 61 wt % host mixture

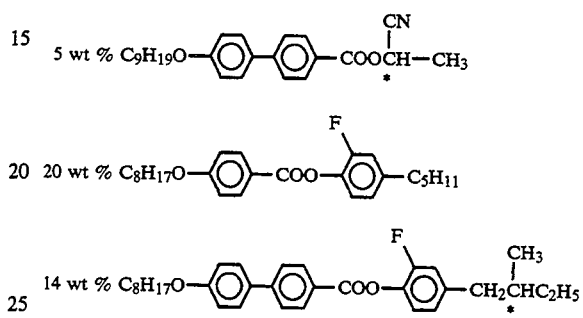

5 wt % $C_9H_{19}O$—〇—〇—COOCH(CN)—CH$_3$ 20 wt % $C_8H_{17}O$—〇—COO—〇(F)—C$_5H_{11}$ 14 wt % $C_8H_{17}O$—〇—〇—COO—〇(F)—CH$_2$CH(CH$_3$)C$_2$H$_5$

In this mixture the two optically active compounds induced the appearance of Ch phases of opposite helical twist sense and hence the mixture is pitch compensated.

Transition temperatures: S$_C$—S$_A$ 63.4°, S$_A$—N 84.2°, N—Ch 100°, Ch—I 120.4°–122.2 (room temperature S$_C$).

| Ferroelectric properties | | | |
|---|---|---|---|
| Temperature °C. | Ps nCcm$^{-2}$ | Temperature °C. | Ps nCcm$^{-2}$ |
| −10 | 22.22 | 30 | 13.54 |
| −5 | 21.52 | 35 | 11.81 |
| 0 | 19.44 | 40 | 10.94 |
| 5 | 18.40 | 45 | 9.54 |
| 10 | 17.36 | 50 | 8.16 |
| 15 | 16.67 | 55 | 6.42 |
| 20 | 15.28 | 60 | 3.96 |
| 25 | 14.24 | 63 | 0.28 |

EXAMPLE 5

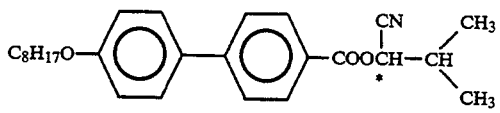

$C_8H_{17}O$—〇—〇—COOCH(CN)—CH(CH$_3$)$_2$

Step 4(1)

A cold solution of sodium nitrite (26.4 g, 0.384 mol) in water (105 ml) was added dropwise to a stirred and cooled solution of L-valine (30.0 g, 0.256 mol) in 0.5 M sulphuric acid (390 ml) during 3 hours, maintaining the temperature between 0° C. and −2° C. The reaction mixture was left stirring at room temperature overnight, then adjusted to pH 6 by adding solid sodium bicarbonate. The solution was concentrated under reduced pressure at 50° C. to about 150 ml. The solution was acidified to pH 3 with 40% H$_3$PO$_4$ and the crude product was extracted into THF (2×200 ml). The THF solutions were washed with brine, dried (Mg SO$_4$) and concentrated under reduced pressure at 50° C. to give an oil.

The crude product was taken in water (105 ml) and decolourized with charcoal at room temperature. A concentrated solution of sodium hydroxide was added dropwise to the cold solution adjusting the pH to 4.5-5. Acetone (3 times the volume of the aqueous solution) was added and the precipitate which formed was filtered off and dried (in vacuo CaCl₂).

yield =22 g (61%) $[\alpha]_D^{20}=-13.95°$ (H₂O).

Step 4(2)

A mixture of the product of step 4(1) (10.0 g 72 mmol), benzyl bromide (12.2 g 72 mmol) and sieve dried DMF (120 ml) was stirred at room temperature for 24 hours. The DMF was removed under reduced pressure (at 50°-55° C.) and the remaining suspension was diluted with ether (100 ml) and filtered. The filtrate was washed successively with water, sodium bicarbonate solution, water, and dried (MgSO₄). After distilling off the solvent (below 55° C.) the crude product was obtained.

yield=14.4 g (96%).

The crude product was purified by distillation at 135°-140° C./0.6-0.65 mm Hg.

Step 4(3)

To a stirred mixture of 4'-octyloxy-4-carboxylic acid (10.8 g 0.033 mol), the product of step 4(2) (6.9 g 0.033 mol) and N—PPY (0.49 g 0.033 mol) in sieve-dried dichloromethane was slowly added a solution of DCC (7.5 g 0.036 mol) in sieve-dried dichloromethane (50 ml) over a period of 20 min.

The reaction mixture was stirred for 6 hours at room temperature. The N,N-dicyclohexylurea was filtered off and the filtrate was washed successively with water, 5% aqueous acetic acid, water and finally dried (MgSO₄). After removal of the solvent, the crude diester was purified by column chromatography using silica gel with 4:1 dichloromethane:light petroleum (bp 60°-80° C.) as eluent, to give a viscous liquid product.

yield=12.5 g (74%).

Step 4(4)

The product of step 4(3) (12.5 g 24.2 mmol) was dissolved in ethyl acetate (160 ml) and 5% Pd on charcoal (200 mg) was added. The mixture was stirred overnight under an atmosphere of hydrogen (the reaction was monitored by TLC). After hydrogenolysis was complete (ca 550 ml of H₂), the catalyst was filtered off and the filtrate was evaporated to dryness to give a solid product. The solid gave a single spot on TLC and was used without further purification.

yield=9.7 g (95%) mp=80°-83° C.

Step 4(5)

The carboxylic acid from 4(4) (9.4 g 22.06 mmol) was initially converted into the acid chloride by reacting with oxalyl chloride (5.75 g 44 mmol) and sieve dried DMF (2 drops) in sodium—dried benzene (25 ml) for 3 hours at room temperature. The excess of oxalyl chloride and the solvent were removed by distillation under reduced pressure. The crude acid chloride was dissolved in diglyme (10 ml) and added to an aqueous solution of ammonia (5 g=0.88, 100 ml) with stirring. After the addition the reaction mixture was stirred for ½ hour at room temperature, then the product was filtered off, washed with water and dried (in vacuo CaCl₂).

yield=9.4 g (100%) mp=95°-97° C.

Step 4(6)

A mixture of thionyl chloride (26.3 g 221 mmol) and sieve-dried DMF (100 ml) was added dropwise during 30 minutes to a vigorously stirred solution of the amid from step 4(5) (9.0 g, 22.1 mmol) in sieve-dried DMF (100 ml). After the addition the reaction mixture was left stirring at room temperature for 8 hours, was then poured onto ice-water and the product was extracted into ether (2×300 ml). The ether extracts were washed successively with a saturated solution of sodium bicarbonate and water, and then dried (MgSO₄). After After removal of the solvent the product was purified by column chromatography on silica gel, eluting with 1:3 ethyl acetate: light petroleum (bp 40°-60° C.).

yield=8.3 g (97%).

The product from the column was recrystallised from light petroleum (bp 40°-60° C.) to give a white crystalline solid.

mp=66.9° C. $[\neq]_D^{20}=-3.1°$ (CHCl₃).

The compounds listed below were prepared using an identical method with the appropriate carboxylic acid in step 4(3) and the amino acid indicated in step 4(1).

General formula:

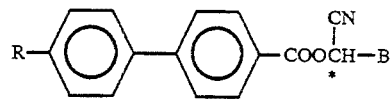

| R | B | $[\alpha]_D^{20}=$ (CHCl₃) | Liquid Crystal Transitions |
|---|---|---|---|
| C₈H₁₇O | CH₂CH(CH₃)₂ | −17.5° | K 46 I |
| (L-Leucine, S-(+)-Leucine) | | | |
| C₈H₁₇O | CH(CH₃)₂ | −3.1° | K 67 I |
| (L-Valine, S-(+)-Valine) | | | |
| C₈H₁₇O | *CH(CH₃)CH₂CH₃ | −5.4° | K 74 I |
| (L-Isoleucine; (2S,3S)-(+)-2-amino-3-methylpentanoic acid) | | | |
| C₈H₁₇O | (CH₂)₃CH₃ | −10.6° | K 59 I |
| (L-Norleucine; (S)-(+)-2-aminohexanoic acid) | | | |

EXAMPLE 6

Preparation of:

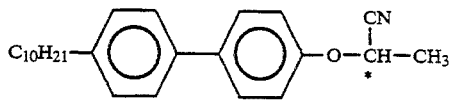

using Route 6.

Step 6(3)

4-n-decyl-4'-hydroxybiphenyl (0.02 mol), tosyl lactate (0.024 mol) and anhydrous potassium carbonate (0.024 mol) in sieve-dried acetonitrile (100 ml) was gently refluxed with vigorous stirring for 20 hr. The cooled reaction mixture was poured into cold water (200 ml) and extracted with ether (2×150 ml). The combined ether extracts were washed with water (100 ml), cold 5% aqueous NaOH (100 ml), water (2×100 ml) and dried (MgSO₄). After removal of the solvent, the solid residue was recrystallised from 95% aqueous ethanol to yield the product as colourless crystals.

Yield 5.5 g (67%), mp 38° C., $[\alpha]_D^{24}+91.1°$ (CHCl₃).

Step 6(4)

The product of step 6(3) (0.012 mol), KOH (0.0144 mol) in water (15 ml) and ethanol (50 ml) was gently refluxed for 1 hr. Excess solvent was removed under reduced pressure and the residue was diluted with cold water (50 ml) and them carefully acidified by the addition of dilute HCl until a pH of about 2 was obtained. The mixture was extracted with ether (3×50 ml) and the combined ether extracts were washed with water (50 ml) and dried (MgSO$_4$). After removal of the solvent, the solid residue was recrystallised from petroleum ether (80°–100° C.).

Yield 4.3 g (93%), mp 110.5° C., $[\alpha]_D^{24}$+8.4° (CHCl$_3$).

Step 6(5)

This was carried out using a similar method to that of Route 1 step 4. The starting materials were the product of step 6(4) (0.011 mol), oxalyl chloride (0.021 mol) in benzene (60 ml), DMF (2 drops) and 35% aq. NH$_3$ in diglyme (100 ml). The crude product was crystallised from petroleum ether (100°–120° C.).

Yield 3.6 g, (88%), mp 171° C.

Step 6(6)

This was carried out using a method similar to that of Route 1 step 5. The starting materials were the product of step 6(5) (0.0087 mol), thionyl chloride (0.0087 mol) in DMF (80 ml). The crude product was chromatographed using silica gel and eluted with CH$_2$Cl$_2$. The purified material was crystallised from ethanol.

Yield 2.6 g, (84%), mp 66° C., $[\alpha]_D^{24}$+96.8° (CHCl$_3$).

EXAMPLE 7

Using the methods outlined in the description above the following compounds were also prepared:

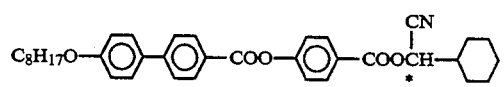

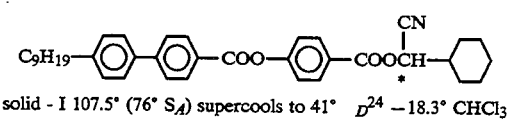

solid - I 107.5° (76° S$_A$) supercools to 41° $_D^{24}$ −18.3° CHCl$_3$

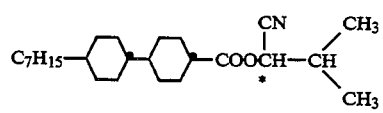
A.

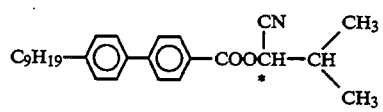
B.

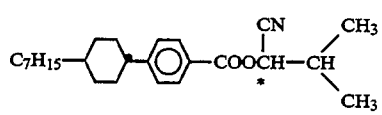
C.

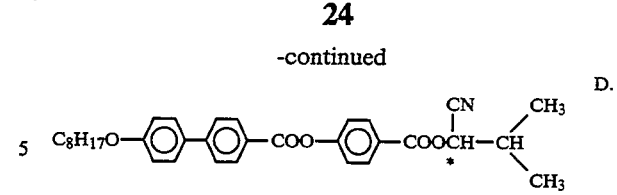
D.

Some of their properties are listed below:
A. solid—isotropic 84.3°, $[\alpha]_D$°—28.1 (CHCl$_3$)
B. solid$^1$—solid$^2$ 29.4°, solid—isotropic 32.2° $[\alpha]_D^{20}$−4.8° (CHCl$_3$)
C. liquid, mp below −20° C. $[\alpha]_D^{20}$−16.8° (CHCl$_3$)
D. solid—S$_C$ 102°, S$_C$—S$_A$ 145°, S$_A$—I 154.6 $[\alpha]_D^{20}$ −9.35° (CHCl$_3$).

EXAMPLE 8

Ferroelectric smectic liquid crystal mixtures containing compounds of formula I and 4.1.

In the data below, the material H1 has a composition:

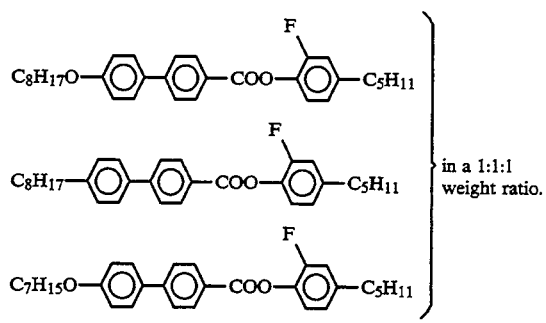

in a 1:1:1 weight ratio.

and the nematic material E7 has a composition:

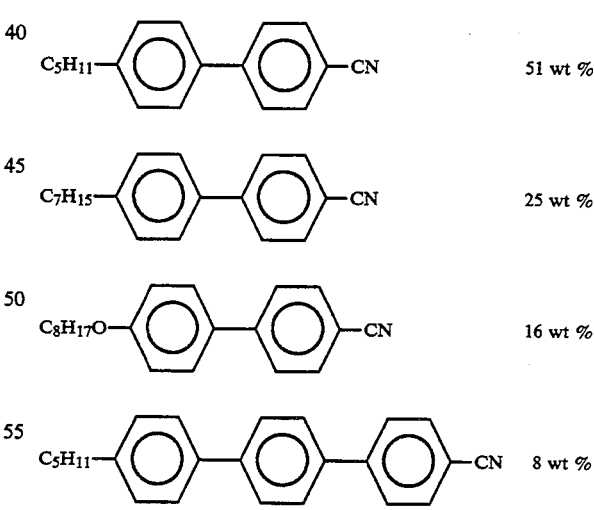

Properties of mixtures containing compounds of formula I and H1 are listed in tables 5 and 6 where the following symbols and abbreviations are used
Ps=extrapolated spontaneous polarisation (nCcm$^{-2}$)
N*p=chiral nematic pitch in E7 (μm)
pPs=N*p×Ps
SOP/$s_{ON}$=sense of N* helical pitch and polarisation of S$_C$* phase
C9, C9O etc. are abbreviations for C$_9$H$_{19}$, C$_9$H$_{19}$O etc.

TABLE 5

| Structure | $P_S$ nCcm$^{-2}$ | N* p μm | pP$_S$ | SOP/ SON* | Trans. Temps. (10% in H1) N S$_A$ | S$_C$ | S$_7$ |
|---|---|---|---|---|---|---|---|
| C$_9$—⌬—⌬—CO$_2$C*HC$_1$ / CN | 180 | 0.20 | 36 | L+ | 112 | 67 | 40 |
| C$_9$O—⌬—⌬—CO$_2$C*HC$_1$ / CN | 137 | | | L+ | 115 | 81 | 33 |
| C$_9$O—⌬—⌬—CO$_2$—⌬—CO$_2$C*HC$_1$ / CN | 70 | 0.58 | 41 | L+ | 133 | 78 | 49 |
| C$_8$O—⌬—⌬—CO$_2$C*HC$_4$ / CN | 139 | 0.27 | 38 | D+ | 112 | 72 | 25 |
| C$_8$O—⌬—⌬—CO$_2$C*HCHC$_1$ / CN C$_1$ | 164 | 0.53 | 87 | D+ | 111 | 74 | 23 |
| C$_8$O—⌬—⌬—CO$_2$C*HCH$_2$CHC$_1$ / CN C$_1$ | 125 | 0.22 | 28 | D+ | 110 | 59 | 27 |
| C$_8$O—⌬—⌬—CO$_2$C*HC*HCH$_2$C$_1$ / CN C$_1$ | — | 0.15 | — | D | | | |
| C$_8$O—⌬—⌬—CO$_2$C*H—cyclohexyl / CN | 112 | 0.60 | 67 | D+ | 105 | 58 | 22 |
| C$_9$—⌬—⌬—CO$_2$—⌬—CO$_2$C*H—cyclohexyl / CN | | | | D+ | 128 | 63 | 45 |
| C$_{10}$—⌬—⌬—OC*HC$_1$ / CN | 2.5 | 0.68 | 2 | + | 101 | 80 | 37 |

Table 6 below shows properties of fast switching ferroelectric smectic liquid crystal mixtures based upon the following materials:

host = H1

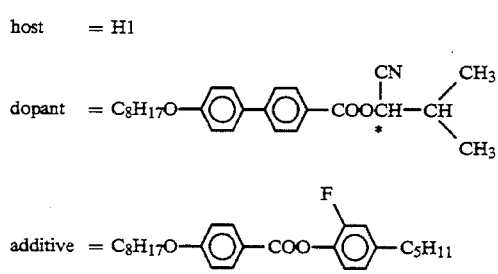

-continued

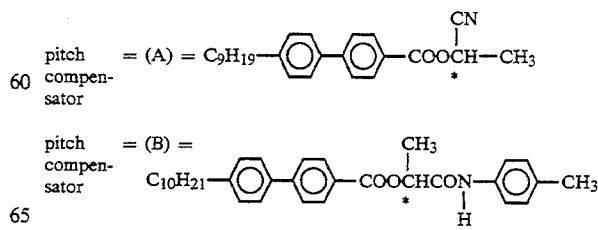

In table 6 proportion of host etc are in weight %, phase transition in °C., tilt in °, PW means minimum pulse width *us) to switch, and AC means the peak voltage to latch (V), Ps and tilt are at 25° C.

Table 6 demonstrates the fast switching time of the mixtures by the low values of the minimum pulse width to switch.

Figure 7:
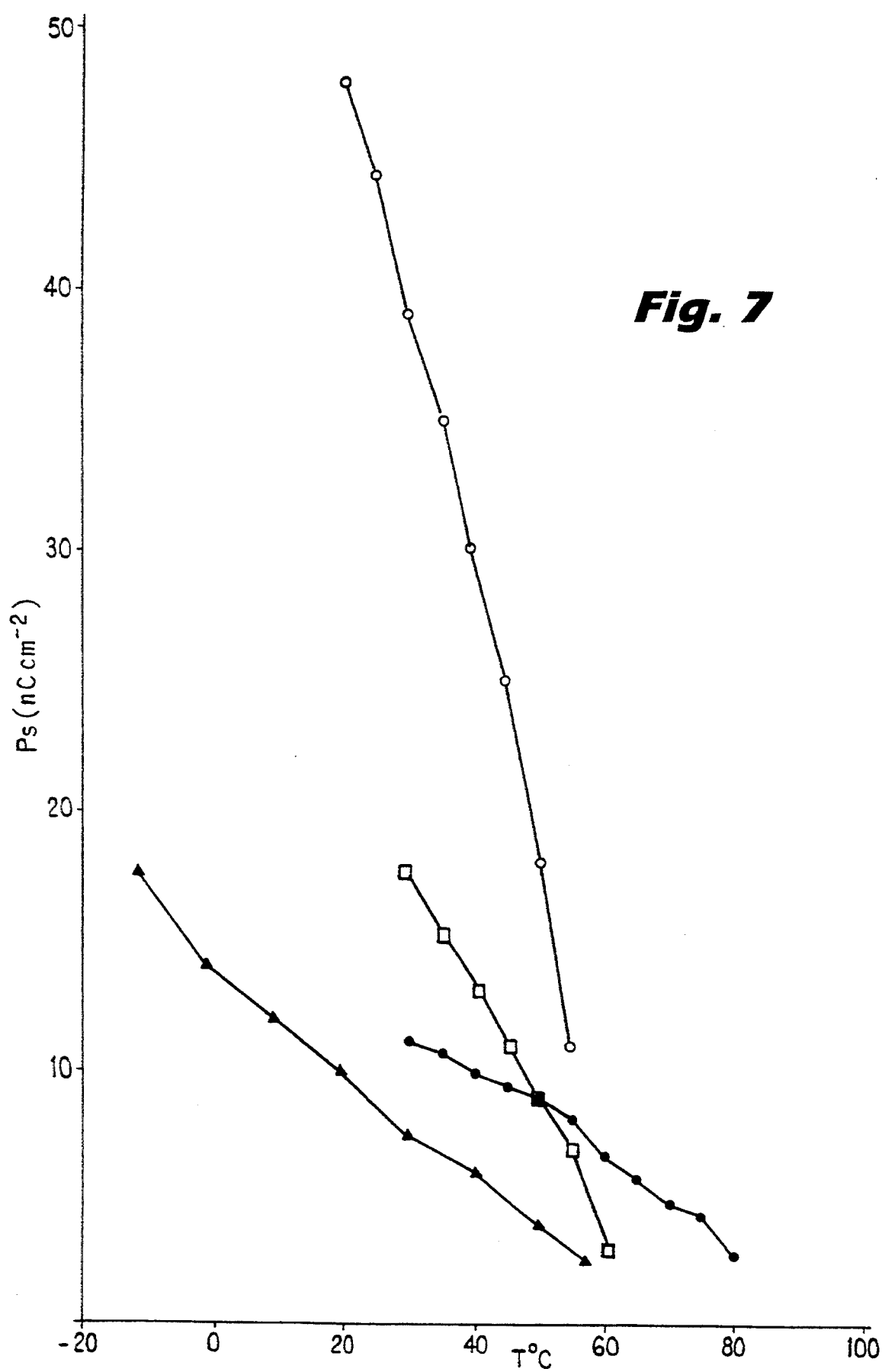
FIG. 7 graphs of Ps against temperature for mixtures of the invnetion.

FIG. 7 shows graphs of Ps against temperature (°C.) for various of the mixtures listed in table 6. The symbols in table 6 identify the graphs.

EXAMPLE 9

Ferroelectric smectic liquid crystal mixtures containing compounds of formula I and 4.3.

A mectic host H2 was prepared having a composition:

$C_4H_9O$—◯—◯—◯—$C_5H_{11}$ (with F substituent)  32.5 wt %

$C_8H_{17}O$—◯—◯—◯—$C_5H_{11}$ (with F substituent)  29.5 wt %

$C_6H_{13}O$—◯—◯—◯—$C_5H_{11}$ (with F substituent)  22.0 wt %

$C_{10}H_{21}$—◯—◯—◯—$C_5H_{11}$ (with F substituent)  16.0 wt %

$C_4H_9$—◯—◯($C_7H_{15}$)(CN)  5.5 wt %

$C_9H_{19}$—◯—◯—◯(Cl)—OCHCOOC$_2$H$_5$ (CH$_3$)  4.5 wt %

$C_{10}H_{21}O$—◯—◯—COOCH—CH$_3$ (CN)  10 wt %

The configuration of the two optically active compounds was chosen to be such that they induced the appearance of chiral smectic phases of opposite helical twist sense.

The mixture had phase transitions (°C.)
I 145 N* 114 S$_A$ 59.7 S$_C$* 10 S$_?$.

An example of the use of a compound of Formula I in a liquid crystal material and device embodying the present invention will now be described with reference to FIG. 8.

Figure 8:
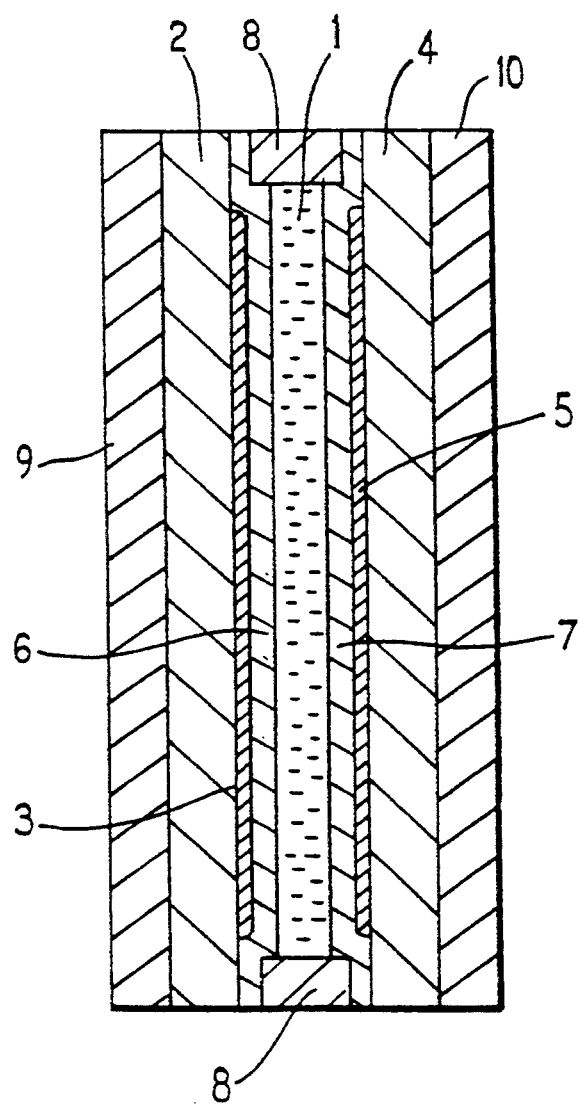
FIG. 8 a liquid crystal device.

In FIG. 8 a liquid crystal cell comprises a layer 1 of liquid crystal material exhibiting a chiral smectic phase sandwiched between a glass slide 2 having a transparent conducting layer 3 on its surface, e.g. of tin oxide or indium oxide, and a glass slide 4 having a transparent conducting layer 5 on its surface. The slides 2,4 bearing the layers 3,5 are respectively coated by films 6,7 of a

TABLE 6

| H1 % | Addv % | Dop % | I | N | SA | SC | S | Ps | Tilt | PW | AC |
|---|---|---|---|---|---|---|---|---|---|---|---|
| 88.75 | 10 | 1.25 | 139 | 89 | 84 |  | 5 | 25 | — | — |  |
| • 87.5 | 10 | 2.5 | 136 | 92 | 83 | 8 |  | 10 | 29 | 130 | 16 |
| 85 | 10 | 5 | 132 | 96 | 75 | 0.5 |  | 21 | 23 | 150 | 30 |
| ○ 80 | 10 | 10 | 126 | 97 | 55 | −2 |  | 36 | 21 | 50 | 40 |
| ☐ 75 | 20 | 5 | 120 | 73 | 60 | −25 |  | 20 | 21 | 60 | 20 |
| 72.5 | 25 | 2.5 | 118 | — | 56 |  |  | 8 | 27 | 500 | 15 |
| 77 | 20 | 3 | 123 | 73 | 66 |  |  | 12 | — | 100 | 16 |
| 85$^a$ | — | 10 | 129 | 106 | 55 | 24 |  | 44 | — | — | — |
| 79$^b$ | 11 | 6.25 | 123 | 92 | 57 |  |  | 26 | 22 | 60 | 40 |
| 80$^c$ | 10 | 9.5 | 124 | 95 | 60 | 2 |  | 35 | 21 | 50 | — |

$^a$plus 5 wt % of compensator A
$^b$plus 3.75 wt % of compensator A
$^c$plus 0.5 wt % of compensator B Mixture H H2  75 wt %

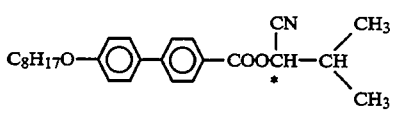

$C_8H_{17}O$—◯—◯—COOCH—CH(CN)(CH$_3$)(CH$_3$)  5 wt %

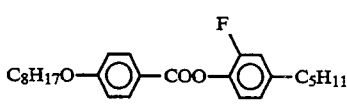

$C_8H_{17}O$—◯—COO—◯(F)—$C_5H_{11}$  20 wt % has phase transitions (°C.)
I 128 N* 84 S$_A$ 64 S$_C$* < −20.

Mixture I

H2  80 wt % polyimide polymer. Prior to construction of the cell the films 6 and 7 and rubbed with a soft tissue in a given direction the rubbing directions being arranged parallel upon construction of the cell. A spacer 8 e.g. of polymethyl methacrylate, separate the slides 2, 4 to the required distance, e.g. 5 microns.

The liquid crystal material 1 is introduced between the slides 2,4 by filling the space between the slides 2, 4 and spacer 8 and sealing the spacer 8 in a vacuum in a known way. Preferably the liquid crystal material is in the smectic A, nematic or isotropic liquid phase (obtained by heating the material) when it is introduced between the slides 2,4 to facilitate alignment of the liquid crystal molecules with the rubbing directions on the slides 2,4.

A polarizer 9 is arranged with its polarization axis parallel to the rubbing direction on the films 6,7 and an analyzer (crossed polarizer) 10 is arranged with its polarization axis perpendicular to that rubbing direction.

When a square wave voltage (from a conventional source not shown) varying between about +10 volts and −10 volts is applied across the cell by making contact with the layers 3 and 5 the cell is rapidly switched upon the change in sign of the voltage between a dark state and a light state as explained above.

In an alternative device (not shown) based on the cell construction shown in FIG. 8 the layers 3 and 5 may be selectively shaped in a known way, e.g. by photoetching or deposition through a mask, e.g. by photoetching or deposition through a mask, e.g. to provide one or more display symbols, e.g. layers, numerals, words or graphics and the like as conventionally seen on displays. The electrode portions formed thereby may be addressed in a variety of ways which include multiplexed operation.

The liquid crystal material 1 may be any one of the mixtures described in the preceding examples.

We claim:

1. An optically active dopant suitable for inclusion in a ferroelectric smectic liquid crystal mixture, said dopant having the structure $$X-COO-\underset{*}{\overset{CN}{\underset{|}{CH}}}-B \qquad \text{Formula I}$$

in which X is a group having the formula:

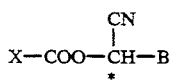

where R is selected from hydrogen, or $C_{1-12}$ alkyl or alkoxy, each of the rings D is the same or different and are independently selected from phenyl and halogen substituted phenyl, A is selected from phenyl, halogen and substituted phenyl and trans-cyclohexyl, d is 0 to 1, and B is selected from $C_{1-12}$ straight chain or branched chain alkyl and alkyl alicyclic.

2. The optically active dopant according to claim 1 where X is

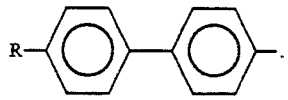

3. The optically active dopant according to claim 2 where B is:

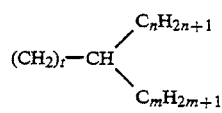

where t is 0 and an integer 1-6, and n and m are the same or different and have values 1-6.

4. The optically active dopant according to claim 2 where B is straight chain alkyl.

5. The optically active dopant according to claim 4 where said straight chain alkyl is $CH_3$.

6. The optically active dopant according to claim 2 where B is

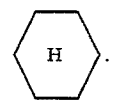

7. The optically active dopant according to claim 1 having the structure

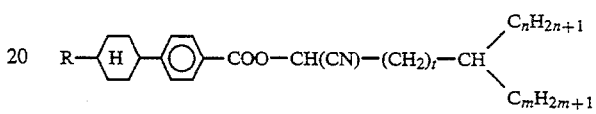

where t is 0 or an integer 1-6, and n and m are the same or different and have values 1-6.

8. A ferroelectric smectic liquid crystal material being a mixture of at least two compounds where at least one compound is a compound according to claim 1 and the other compound selected from:

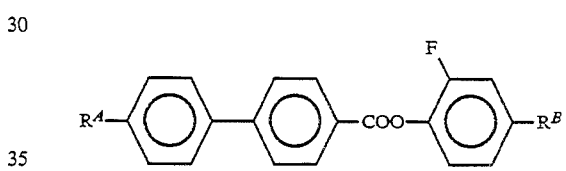

and

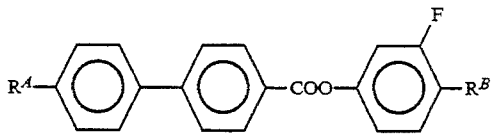

where $R^A$ and $R^B$ are independently $C_{1-12}$ n-alkyl or n-alkoxy or an optically active alkyl or alkoxy group.

9. A ferroelectric smectic liquid crystal material being a mixture of at least two compounds where at least one compound is a compound according to claim 1 and the other compound has the formula:

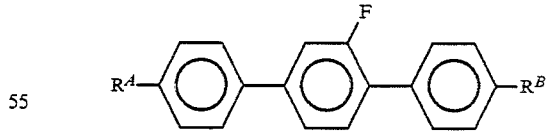

where $R^A$ and $R^B$ are independently $C_{1-12}$ n-alkyl or n-alkoxy.

* * * * *